United States Patent [19]

Kelner et al.

[11] Patent Number: 5,786,210
[45] Date of Patent: Jul. 28, 1998

[54] MAMMALIAN THYMOKINE GENES

[75] Inventors: Gregory S. Kelner, Cupertino; Jacqueline L. Kennedy, Sunnyvale; Albert Zlotnik, Palo Alto, all of Calif.

[73] Assignee: Schering Corporation, Kenilworth, N.J.

[21] Appl. No.: 329,704

[22] Filed: Oct. 25, 1994

Related U.S. Application Data

[63] Continuation-in-part of Ser. No. 231,421, Apr. 22, 1994, abandoned, which is a continuation-in-part of Ser. No. 193,483, Feb. 8, 1994, abandoned.

[51] Int. Cl.$^6$ ................................................. C07H 21/04
[52] U.S. Cl. .................... 435/320.1; 536/23.5; 435/325; 435/252.3; 935/9
[58] Field of Search ......................... 536/23.5; 530/350, 530/351; 435/69.1, 69.5, 172.1, 240.2, 252.3, 320.1, 325; 930/140; 935/9

[56] References Cited

PUBLICATIONS

Dale I. Godfrey, et al., "A Developmental Pathway Involving Four Phenotypically and Functionally Distinct Subsets of $CD3^-CD4^-CD8^-$ Triple-Negative Adult Mouse Thymocytes Defined by CD44 and CD25 Expression," *J. Immunol.*, 150:4244–4252, May 1993.

Dale I. Godfrey, et al., "Phenotypic and Functional Characterization of c-kit Expression During Intrathymic T Cell Development," *J. Immunol.*, 149:2281–2285, Oct. 1992.

Alice Suk Yue Ho, et al., "A Receptor for Interleukin 10 Is Related to Interferon Receptors," *PNAS USA*, 90:11267–11271, Dec. 1993.

Gregory S. Kelner, et al., "Lymphptactin: A Cytokine That Represents a New Class of Chemokine," *Science*, 266:1395–1399, Nov. 25, 1994.

Kouji Matsushima, et al., "Interleukin 8 and MCAF: Novel Inflammatory Cytokines Inducible by IL 1 and TNF," *Cytokine*, 1:2–13, Nov. 1989.

Michael D. Miller, et al., "The Human Cytokine I–309 Is a Monocyte Chemoattractant," *PNAS USA*, 89:2950–2954, 1992.

Joost J. Oppenheim, et al., "Properties of the Novel Proinflammatory Supergene 'Intercrine' Cytokine Family," *Annu. Rev. Immunol.*, 9:617–648, 1991.

Thomas J. Schall, "Biology of the RANTES/SIS Cytokine Family," *Cytokine*, 3:165–183, May 1991.

Thomas J. Schall, "The Chemokines," *The Cytokine Handbook*, Academic Press, NY, preprint of chapter.

Brian Seed, et al., "Molecular Cloning of the CD2 Antigen, the T–cell Erythrocyte Receptor, by a Rapid Immunoselection Procedure," *PNAS USA*, 84:3365–3369, May 1987.

Alan R. Shaw, "Molecular Biology of Cytokines: An Introduction," Chapter 2, Title Page, Verso and Table of Contents, in *The Cytokine Handbook*, edited by Angus W. Thomson, Academic Press Inc., San Diego, CA, 1991.

Takashi Suda, et al., "IL–7 Maintains the T Cell Precursor Potential of $CD3^-CD4^-CD8^-$ Thymocytes," *J. Immunol.*, 146:3068–3073, May 1991.

Mark Y. Stoeckle, et al., "Two Burgeoning Families of Platelet Factor 4–Related Proteins: Mediators of the Inflammatory Response," *The New Biologist*, 2:313–323, Apr. 1990.

Albert Zlotnik, et al., "Cytokine Production by Mature and Immature $CD4^-CD8^-$ T Cells $\alpha\beta$–T Cell Receptor$^+$ $CD4^-CD8^{-T\ Cells\ Produce\ IL-4}$," *J. Immunol.*, 149:1211–1215, Aug. 1992.

Sabine Müller, et al., "Clonig of ATAC, an Activation–Induced, Chemokine–Related Molecule Exclusively Expressed in $CD8^+$ T Lymphocytes," *Eur. J. Immunol.* 25:1744–1748, 1995.

Tetsuya Yoshia, et al. "Molecular Cloning of a Novel C or $\gamma$ Type Chemokine, SCM–1" *FEBS Letts.* 360:155–159, 1995.

*Primary Examiner*—Stephen Walsh
*Assistant Examiner*—Lorraine Spector
*Attorney, Agent, or Firm*—Jonathan A. Quine; Kenneth A. Weber; Edwin P. Ching

[57] ABSTRACT

Nucleic acids encoding a thymokine from a mammal, reagents related thereto, including specific antibodies, and purified proteins are described. Methods of using said reagents and related diagnostic kits are also provided.

6 Claims, 1 Drawing Sheet

```
Exon 1   Gro    M I P A T R S L L C A A L L L L A T S R L A T G
         LTn           M R L L L T F L G V C C L T P W V V
         Mip-1       M K L C V S A L S L L L V A A F C A P G F S Exon 2   Gro        A P I A N E L R C Q C L Q T M A . G I H L K N I Q S L K V L P S G P H C T Q T
         LTn    E G V G T E V L E E S S C V N L Q T Q R L P V Q K T I I W E G . . . A M R
         Mip-1  A P M G S D P P T S C C F S Y T A R K L P R N F V V D Y Y E T S S L . . C S Q P Exon 3   Gro    E V I A T L K N G R E A C L D P E A P L V Q K I V Q K M L K G V P K
         LTn    A V I . T K R G L K I C A D P E A K W V L A A I K T V D G R A S T R K N M A E T V P G T G A Q R S T S T A I T L T G
         Mip-1  A V V Q T K R S K Q V C A D P S E S W V Q E Y V Y D L E L N . .
```

Figure 1

MAMMALIAN THYMOKINE GENES

This application is a continuation-in-part of U.S. Ser. No. 08/231,421 file Apr. 22, 1994, since abandoned which is a continuation-in-part of then U.S. Ser. No. 8/193,483, filed Feb. 8, 1994, since abandoned. Each of these applications are incorporated herein by reference in their entireties.

FIELD OF THE INVENTION

The present invention contemplates compositions related to proteins which function in controlling development, differentiation and physiology of mammalian cells, e.g., cells of a mammalian immune system. In particular, it provides proteins which regulate or evidence development, differentiation, and function of various cell types, including hematopoietic cells.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed.) (1993) *Fundamental Immunology* (3d ed.) Raven Press, N.Y. Myeloid cell production occurs through the differentiation and later commitment of myeloid progenitor cell lineages. Progression through terminal stages of differentiation is regulated by various signals provided to the cells, only a fraction of which have been identified. The resulting cells primarily fall into either the B cell subset or the T cell subset. The development of the T cell subset is generally believed to be closely linked to the thymus, which provides an appropriate environment for development and differentiation of T cell precursors. Differentiation from multipotent stem cells to committed T cell precursors and development to functionally mature T cells provides various T cell subsets exhibiting specialized immunological functions. These differentiation and developmental processes appear to occur throughout the lifetime of an individual.

The thymus contains a rare population of primitive pluripotent progenitor cells, e.g., stem cells, that have the capacity to differentiate into any mature T cell later found in the peripheral circulation. Stem cells can either proliferate and generate cells with nearly the identical capacity (self-renewal) or start down a differentiation pathway of becoming more restricted in the production of particular cell types, eventually becoming a cell with a highly specialized function.

The immediate precursors of T cell progenitors are of particular interest because they can serve as a reserve of cells available for differentiation to more mature T cells when necessary or appropriate. Such needs may arise from blood loss, short- or long-term immunocompromised conditions or similar problems, e.g., as a result of chemo- or radiation-therapy. Alternatively, conditions of excessive T cell production, e.g., myeloid cell proliferative disorders, may result from abnormal regulation by factors which promote cellular development.

Many factors have been identified which influence the differentiation process of precursor T-cells, including the cytokines c-kit ligand, IL-4, and IL-7. See, e.g., Godfrey, et al (1992) *J. Immunol.* 149: 2281–2285; and Suda and Zlotnik (1991) *J. Immunol.* 146: 3068–3073. These cytokines stimulate early stages of myeloid cell differentiation in vitro, but only the latter have been shown to be necessary for stimulating T cell differentiation in vivo.

These observations indicate that other factors exist whose functions in hematopoiesis were heretofore unrecognized. These factors provide for biological activities whose spectra of effects are distinct from known differentiation or activation factors. The absence of knowledge about the structural, biological, and physiological properties of the regulatory factors which regulate T cell physiology in vivo prevents the modification of the effects of such factors. Thus, medical conditions where regulation of the development or physiology of relevant cells is required remains unmanageable.

The chemokines are a large and diverse superfamily of proteins. The superfamily is subdivided into two branches, based upon whether the first two cysteines in the chemokine motif are adjacent (termed the "C-C" branch) or spaced by an intervening residue ("C-X-C"). See Lindley et al. *Immunology Today* 14, 24 (1993). The present invention reveals the existence of a previously unknown class of chemokines which are hereby termed thymokines. The thymokines have only a single cysteine in the corresponding region of the chemokine motif. Based on both chromosome mapping and sequence analysis of the two lymphotactin protein thymokines described below, we show that the thymokines do not belong to the C-C or C-X-C chemokine family. They represent the first known member of a new class of chemokines designated thymokines, or alternatively, the C family of chemokines. Chemotactic studies are presented which suggest that the lymphotactin thymokines exhibit functions which are specific for lymphocytes. As such, they are the first example of lymphocyte-specific chemokines.

SUMMARY OF THE INVENTION

The present invention is based, in part, upon the discovery of a new family of genes termed thymokines which encode proteins with distant similarity to the C-C and CXC chemokines. Thymokines were originally found in subsets of cells found in the thymus. These subsets were isolated based upon their expression of cell surface molecules, which indicated that these T cells, (i.e., CD44$^+$CD25$^+$CD3$^-$CD4$^-$CD8$^-$ thymocytes) were undergoing critical stages in differentiation or which represent other specific lineages of T cells whose functions remain undefined, (i.e., CD4$^-$CD8$^-$ αβTcR$^+$T cells). The Thymokine genes and proteins presented herein define a heretofore unidentified class of small chemokine-like proteins.

The present invention provides methods of modulating physiology or development of a cell comprising contacting said cell with an agonist or antagonist of a thymokine. In preferred embodiments, the antagonist is an antibody which specifically binds to a mammalian thymokine, such as human lymphotactin, or mouse lymphotactin.

The present invention describes a nucleic acid encoding a mammalian thymokine or fragment thereof. Several specific embodiments are described in the detailed description and the examples, including the naturally occurring mouse and human lymphotactin proteins and nucleic acid sequences, and genetically engineered thymokine nucleic acids which were altered to create specific cloning sites. As described herein, these molecules all share similar biological properties, including the mouse and human lymphotactin molecules, which are only about 60% identical at the amino acid level. Preferably, the nucleic acids of the invention comprise a sequence of at least 25 nucleotides at least 90% similar to a sequence of SEQ ID NO 1 or SEQ ID NO 3; at least 50 nucleotides at least 80% similar to a sequence of SEQ ID NO 1 or 3 at least 90% similar to the sequence of SEQ ID NO 1 from nucleotide 32 to 352; at least 90% similar to the sequence of SEQ IN NO 3 from nucleotide 15 to 334; at least 90% similar to the sequence of SEQ ID NO 1 from nucleotide 92 to 352; at least 90% similar to the sequence of SEQ ID NO 3 from nucleotide 75 to 334; encoded by the coding region of the insert in clone m3C9; or encoded by the coding region of the insert in clone A 10-4.

In other embodiments, the invention provides an antibody which specifically binds to a thymokine. In various embodiments, the thymokine is a mammalian protein, including mouse and human proteins; the antibody is raised against a peptide of at least 10 amino acids with a sequence of SEQ ID NO 2 or SEQ ID NO 4; the antibody is a monoclonal antibody; or the antibody is labeled.

The invention also provides a substantially pure thymokine or peptide fragment thereof, or a fusion protein comprising thymokine sequence. In various embodiments, the thymokine or peptide fragment thereof is from a warm blooded animal selected from the group of birds and mammals, including humans and mice; the polypeptide comprises at least one polypeptide segment of at least 15 amino acids from SEQ ID NO 2 or SEQ ID NO 4; a polypeptide comprising a sequence exhibiting at least 90% identity to a protein sequence from amino acid 1 to 19 of SEQ ID NO 2; a polypeptide comprising a sequence exhibiting at least 90% identity to a protein sequence from amino acid 1 to 19 of SEQ ID NO 4; a polypeptide comprising a sequence exhibiting at least 80% identity to a protein sequence from amino acid 21 to 113 of SEQ ID NO 2; a polypeptide comprising a sequence exhibiting at least 80% identity to a protein sequence from amino acid 21 to 11 3 of SEQ ID NO 4; a polypeptide comprising a sequence exhibiting at least 80% identity to a protein sequence from amino acid 56 to 83 of SEQ ID NO 2; a polypeptide comprising a sequence exhibiting at least 80% identity to a protein sequence from amino acid 56 to 83 of SEQ ID NO 4; and the thymokine or peptide exhibits a post-translational modification pattern distinct from natural mammalian thymokines.

Preferably, the thymokine, at the position corresponding to residue 57 of the mouse or human lymphotactin is hydrophobic, e.g., alanine; to residue 58 is hydrophobic, e.g., valine, leucine, or isoleucine; to residue 59 is hydrophobic, e.g., isoleucine or valine; to residue 60 is phenylalanine; to residue 62 is an OH containing residue, e.g., threonine or serine; to residue 63 is hydrophilic (lysine or arginine); to residue 64 is hydrophilic, e.g., lysine or arginine; to residue 65 is glycine; to residue 66 is leucine; to residue 67 is hydrophilic, e.g., lysine, glutamic, or glutamine; to residue 68 is hydrophobic, e.g., isoleucine, valine, or alanine; to residue 69 is cysteine; to residue 70 is alanine; to residue 71 is aspartic; to residue 72 is proline; and corresponding to the mouse lymphotactin, to residue 75 is hydrophilic, e.g., lysine, or arginine; to residue 76 is tryptophan; to residue 77 is valine; to residue 78 is hydrophilic, e.g., lysine, glutamine, or arginine; to residue 84 is hydrophobic, e.g., valine or leucine; and/or to residue 85 is negatively charged, e.g., aspartic or glutamic.

The mouse and human lymphotactin proteins share 60% amino acid identity. It is expected that thymokine proteins derived from animals more closely related to mice, such as other rodents, will have greater sequence similarity to mouse lymphotactin than does the human lymphotactin described herein. Conversely, species more closely related to humans, such as primates, will have thymokine proteins with greater sequence similarity to human lymphotactin than does the described mouse lymphotactin. It should be noted that, despite the evolutionary divergence of mouse and human lymphotactin, the proteins share biological properties.

Other features of the invention provide a kit comprising a nucleic acid encoding a thymokine or peptide fragment thereof; an antibody or receptor which specifically binds a thymokine; or a substantially pure thymokine or fragment thereof. For instance, an antibody is provided which is specifically immunoreactive with a protein encoded by the polypeptide of SEQ ID NO 2 or SEQ ID NO 4. Such kits may also include instructional materials, packaging of components into containers and other similar variants.

The present invention provides an isolated thymokine protein, wherein said thymokine protein specifically binds to an antibody generated against an immunogen such as the polypeptides described by SEQ ID NO. 2 and SEQ ID NO. 4. The thymokine protein induces a dose-dependant chemotactic response by thymocytes in a thymokine cell chemotaxis assay. The thymokine protein does not induce a dose-dependant chemotactic response in human THP-1 cells in the thymokine cell chemotaxis assay, nor does it induce an intracellular $Ca^{+2}$ flux in human THP-1 cells in an intracellular $Ca^{+2}$ flux assay. The cell chemotaxis assay and the intracellular $Ca^{+2}$ assays are described in detail in the examples below. Particularly preferred thymokine proteins include mouse lymphotactin and human lymphotactin, as depicted, e.g., in SEQ ID NO 2 and SEQ ID NO 4. The thymokine protein may be recombinantly produced or naturally occurring.

This invention also provides for an isolated nucleic acid encoding a thymokine protein. The nucleic acid is capable of selectively hybridizing to either the nucleic acid shown in SEQ ID NO 1, or SEQ ID NO. 3, in the presence of competitive DNA such as a human genomic library, under stringent hybridization conditions. For instance the nucleic acid encoding a thymokine protein selectively hybridizes to the nucleotide sequence of SEQ ID NO 3 under hybridization conditions of 42° C. and 50% formamide and stays bound to the nucleic acid of SEQ ID NO 3 under wash conditions of 2×SSC and 0.1% SDS at 65° C. for at least 20 minutes. The nucleic acid sequence may encode, e.g., a thymokine polypeptide with complete sequence identity to a naturally occurring thymokine protein. The nucleic acid may also encode a thymokine polypeptide which is not identical to a naturally occurring polypeptide, such as a thymokine fusion protein, or a genetically engineered mutant thymokine protein which retains the bases critical for thymokine function or immunogenicity as described herein.

The present invention provides for an isolated nucleic acid encoding a thymokine protein, wherein the thymokine protein specifically binds an antibody generated against an polypeptide immunogen generated from the polypeptides of SEQ ID NO 2 and SEQ ID NO 4. The isolated nucleic acid includes the nucleic acids of SEQ ID NO 1 and SEQ ID NO 3. The isolated nucleic acid may encode a thymokine polypeptide with complete sequence identity to a naturally occurring thymokine protein, or it may encode a fragment thereof with the immunogenicity specified above. Examples of isolated nucleic acids include the nucleic acid encoding the thymokine proteins which the encompass the polypeptides of SEQ ID NO 2 and SEQ ID NO 4, and the genetically engineered variants thereof described in the examples below.

The isolated nucleic acid encoding the thymokine protein described above may be used to transfect a cell to generate additional copies of the isolated nucleic acid (through cloning, using standard techniques) or to produce the thymokine protein which it encodes (e.g., in a standard expression system). For instance, the cell may be transfected with a polynucleotide sequence such as that depicted in SEQ ID NO 1, or SEQ ID NO 3, or a sequence engineered to facilitate cloning or expression, e.g., as described in the examples below.

This invention provides a method of detecting a thymokine protein in a biological sample by contacting a binding agent having an affinity for a thymokine protein with the biological sample; incubating the binding agent with the biological sample to form a binding agent:thymokine protein complex; and detecting said complex. The biological sample may be derived from any natural or genetically engineered source, such as human or other mammalian tissue, tissue culture or non-mammalian tissue. The binding agent can be, e.g., a monoclonal antibody, a polyclonal antibody, a thymokine binding protein such as a thymokine receptor molecule, or a polymer such as an affinity matrix, carbohydrate or lipid. Detection may proceed by any known method, such as immunoblotting, western analysis, gel-mobility shift assays, fluorescence in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge.

The present invention provides a method for detecting antibodies reactive with a thymokine protein in a biological sample by contacting a composition containing recombinant or isolated thymokine protein with the biological sample; incubating the composition with the biological sample to form an antibody:thymokine protein complex; and detecting the complex, e.g., by the methods described above.

Nucleic acid probes capable of selectively hybridizing to a nucleic acid encoding a thymokine protein are described herein. The nucleic acid probe will bind, e.g., the nucleic acid of SEQ ID NO 1, and/or the nucleic acid of SEQ ID NO 3.

The present invention provides a method of detecting a nucleic acid encoding an thymokine protein in a biological sample by contacting the biological sample with a nucleic acid probe capable of selectively hybridizing to the nucleic acid; incubating the nucleic acid probe with the biological sample to form a hybrid of the nucleic acid probe with complementary nucleic acid sequences present in the biological sample; and determining the extent of hybridization of the nucleic acid probe to the complementary nucleic acid sequences by standard techniques such as Southern analysis, northern analysis and the polymerase chain reaction (PCR). The nucleic acid probe is capable of hybridizing to a nucleic acid encoding a protein such as the polypeptide of SEQ ID NO 2 or the polypeptide of SEQ ID NO 4.

DESCRIPTION OF THE DRAWINGS

FIG. 1 shows a sequence alignment of mouse lymphotactin amino acid sequence (LTn) with the C-X-C chemokine Gro α (Gro) and the C-C chemokine Macrophage inflammatory protein 1β (Mip-1).

DETAILED DESCRIPTION

I. General

The present invention provides DNA sequences encoding mammalian proteins which exhibit structural properties characteristic of a cytokine or chemokine. For a review of the chemokine family, see, e.g., Lodi et al (1994) *Science* 263: 1762–1767; Gronenborn and Clore (1991) *Protein Engineering* 4: 263–269; Miller and Kranger (1992) *Proc. Nat'l Acad. Sci. USA* 89: 2950–2954; Matsushima and Oppenheim (1989) *Cytokine* 1: 2–13; Stoeckle and Baker (1990) *New Biol* 2: 313–323; Oppenheim et al. (1991) *Ann. Rev. Immunol.* 9: 617–648; Schall (1991) *Cytokine* 3: 165–183; and *The Cytokine Handbook* Academic Press, N.Y. These proteins are designated thymokines because they were initially found on subsets of thymus cells, e.g., thymocytes, and characterized as proteins which exhibit structural characteristics of chemokines. The label does not imply that the molecules have direct biological activity on thymocytes. Initial studies localized a thymokine to a subpopulation of cells believed to be primitive uncommitted T-cells progenitors. A separate T cell lineage, the CD4$^-$CD8$^-$ αβ T cell receptor (CD4$^-$CD8$^-$ αβ TCR$^+$) cells also expressed a message encoding this protein. Thus, the gene was independently derived from two different cell subpopulations.

The best characterized embodiment of this family of proteins was discovered in mouse and is designated mouse lymphotactin. An additional thymokine found in humans, designated human lymphotactin is also described herein. The descriptions below are directed, for exemplary purposes, to human and mouse lymphotactin, but are likewise applicable to related embodiments from other sources.

The thymokine proteins of this invention are defined by their physicochemical and biological properties. The biological properties of the mouse and human thymokines described herein, e.g., mouse lymphotactin and human lymphotactin, are defined herein by their size, amino acid sequence and biological properties in specified biological assays. Despite sharing biological properties, the human and mouse lymphotactin molecules are only 60% identical, and thus one of skill will readily recognize that there are a large number of amino acid substitutions, deletions and insertions that can be made without altering significantly the biological activity of the molecule. This disclosure teaches one of skill which amino acids may be changed without affecting the biological activity of the molecule.

Thymokines are present in specific tissue types, and the interaction of the protein with a receptor is important for mediating various aspects of cellular physiology or development. The cellular types which express message encoding thymokines suggest that signals important in cell differentiation and development are mediated by them. See, e.g., Gilbert (1991) *Developmental Biology* (3d ed.) Sinauer Associates, Sunderland, Mass.; Browder et al. (1991) *Developmental Biology* (3d ed.) Saunders, Philadelphia, Pa.; Russo et al (1992) *Development: The Molecular Genetic Approach* Springer-Verlag, New York, N.Y.; and Wilkins (1993) *Genetic Analysis of Animal Development* (2d ed.) Wiley-Liss, New York, N.Y. Moreover, thymokine expression serves as a means to define certain cell subpopulations.

The cytokine producing profile of progenitor T (Pro T) cells is elucidated herein. While screening a cDNA library generated from activated mouse Progenitor T cells, a novel cytokine, designated mouse lymphotactin was discovered. Mouse lymphotactin exhibits distant similarity to members of both the C-C and C-X-C chemokine families, lacking two of the four cysteines characteristic of chemokines. Lymphotactin is abundantly expressed in activated CD8$^+$T-cells and CD4$^-$CD8$^-$ α⊕TCR$^+$thymocytes. Significantly, it has chemotactic activity on lymphocytes but not on monocytes or neutrophils. Unlike C-C or C-X-C chemokine genes, the mouse lymphotactin gene maps to chromosome one, further suggesting that it is evolutionarily distinct from the two known chemokine superfamilies. Taken together, these observations show that thymokine represent a novel addition to the chemokine superfamily.

II. Definitions

The term "binding composition" refers to molecules that bind with specificity to a thymokine, e.g., in a ligand-receptor type fashion, an antibody-antigen interaction, or compounds, e.g., proteins which specifically associate with thymokines. Typically, the association will be in a natural physiologically relevant protein-protein interaction, either covalent or non-covalent, and may include members of a multiprotein complex, including carrier compounds or dimerization partners. The molecule may be a polymer, or chemical reagent. No implication as to whether a thymokine is either the ligand or the receptor of a ligand-receptor interaction is necessarily represented, other than whether the interaction exhibits similar specificity, e.g., specific affinity. A functional analog may be a ligand with structural modifications, or may be a wholly unrelated molecule, e.g., which has a molecular shape which interacts with the appropriate ligand binding determinants. The ligands may serve as agonists or antagonists of the receptor, see, e.g., Goodman et al (eds.) (1990) *Goodman & Gilman's: The Pharmacological Bases of Therapeutics* (8th ed.) Pergamon Press, Tarrytown, N.Y.

The term "binding agent:thymokine protein complex", as used herein, refers to a complex of a binding agent and a thymokine protein that is formed by specific binding of the binding agent to the thymokine protein. Specific binding of the binding agent means that the binding agent has a specific binding site that recognizes a site on the thymokine protein. For example, antibodies raised to a thymokine protein and recognizing an epitope on the thymokine protein are capable of forming a binding agent: thymokine protein complex by specific binding. Typically, the formation of a binding agent-:thymokine protein complex allows the measurement of thymokine protein in a mixture of other proteins and biologics. The term "antibody:thymokine protein complex" refers to a binding agent:thymokine protein complex in which the binding agent is an antibody. The antibody may be monoclonal, polyclonal or even a binding fragment of an anti body.

"Homologous" nucleic acid sequences, when compared, exhibit significant similarity. The standards for homology in nucleic acids are either measures for homology generally used in the art by sequence comparison and/or phylogenetic relationship, or based upon hybridization conditions. Hybridization conditions are described in greater detail below.

An "isolated" nucleic acid is a nucleic acid, e.g., an RNA, DNA, or a mixed polymer, which is substantially separated from other components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule. An isolated nucleic acid will generally be a homogeneous composition of molecules, but will, in some embodiments, contain minor heterogeneity. This heterogeneity is typically found at the polymer ends or portions not critical to a desired biological function or activity.

As used herein, the term "thymokine protein" shall encompass, when used in a protein context, a protein having mouse amino acid sequences shown in SEQ ID NO 2, or SEQ ID NO 4, or a significant fragment of such a protein. It refers to a polypeptide which exhibits similar biological function to mouse or human lymphotactin,.as determined by the assays described in the examples below, and which interact with thymokine specific binding components. These binding components, e.g., antibodies, typically bind to a thymokine with high affinity, e.g., at least about 100 nM, usually better than about 30 nM, preferably better than about 10 nM, and more preferably at better than about 3 nM.

The term "polypeptide" or "protein" as used herein includes a significant fragment or segment of a thymokine, and encompasses a stretch of amino acid residues of at least about 8 amino acids, generally at least 10 amino acids, more generally at least 1 2 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

"Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W. H. Freeman & Co., San Francisco, Calif.; and Cantor and Schimmel (1980) *Biophysical Chemistry* parts 1–3, W. H. Freeman & Co., San Francisco, Calif., As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the protein.

"Substantially pure" typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO 1, or SEQ ID NO 2. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See, Kanehisa (1984) *Nuc. Acids Res.* 12: 203–213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. See, e.g., Wetmur and Davidson (1968) *J. Mol. Biol.* 31: 349–370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions.

Thymokines from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the mouse lymphotactin protein immunogen with the amino acid sequence depicted in SEQ ID NO 2 can be selected to obtain antibodies specifically immunoreactive with thymokine proteins and not with other proteins. These antibodies recognize proteins highly similar to the homologous mouse lymphotactin protein.

III. Nucleic Acids

Mouse thymokine is exemplary of a larger class of structurally and functionally related proteins. These soluble proteins serve to transmit signals between different cell types, e.g., between T cell progenitors and stroma cells. The preferred embodiments, as disclosed, will be useful in standard procedures to isolate genes from other species, e.g., warm blooded animals, such as birds and mammals. Cross hybridization will allow isolation of related proteins from individuals, strains, or species. A number of different approaches are available successfully to isolate a suitable nucleic acid clone based upon the information provided herein. Southern blot hybridization studies have identified homologous genes in human, monkey, rat, dog, cow, and rabbit genomes under hybridization conditions of 65° C., 2×SSC and 0.1% SDS.

Purified protein or defined peptides are useful for generating antibodies by standard methods, as described below. Synthetic peptides or purified protein can be presented to an immune system to generate polyclonal and monoclonal antibodies. See, e.g., Coligan (1991) *Current Protocols in Immunology* Wiley/Greene, NY; and Harlow and Lane (1989) *Antibodies: A Laboratory Manual* Cold Spring Harbor Press, N.Y., which are incorporated herein by reference. Alternatively, a thymokine receptor can be useful as a specific binding reagent, and advantage can be taken of its specificity of binding, for, e.g., purification of a thymokine ligand or receptor.

The specific binding composition can be used for screening an expression library made from a cell line which expresses a thymokine. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding thymokine proteins such as subcloning nucleic acid sequences encoding polypeptides into expression vectors, labelling probes, DNA hybridization, and the like are described generally in Sambrook et al. (1989) *Molecular Cloning—A Laboratory Manual* (2nd ed.) Vol. 1–3, Cold Spring Harbor Laboratory, Cold Spring Harbor Press, N.Y., which is incorporated herein by reference. This manual is hereinafter referred to as "Sambrook et al."

There are various methods of isolating the DNA sequences encoding thymokine proteins. For example, DNA is isolated from a genomic or cDNA library using labelled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding thymokine proteins, or probes can be designed for use in amplification techniques such as PCR, for the isolation of DNA encoding thymokine proteins.

To prepare a cDNA library, mRNA is isolated from cells which expresses a thymokine protein. cDNA is prepared from the mRNA and ligated into a recombinant vector. The vector is transfected into a recombinant host for propagation, screening and cloning. Methods for making and screening cDNA libraries are well known. See Gubler and Hoffman (1983) Gene 25: 263–269 and Sambrook et al.

For a genomic library, the DNA can be extracted from tissue and either mechanically sheared or enzymatically digested to yield fragments of about 12–20 kb. The fragments are then separated by gradient centrifugation and cloned in bacteriophage lambda vectors. These vectors and phage are packaged in vitro, as described in Sambrook et al. Recombinant phage are analyzed by plaque hybridization as described in Benton and Davis (1977) *Science* 196: 180–182. Colony hybridization is carried out as generally described in e.g., Grunstein et al. (1975) *Proc. Natl. Acad. Sci. USA.* 72: 3961–3965.

DNA encoding a thymokine protein can be identified in either cDNA or genomic libraries by its ability to hybridize with the nucleic acid probes described herein, for example in colony or plaque hybridization experiments. The corresponding DNA regions are isolated by standard methods familiar to those of skill in the art. See Sambrook et al.

Various methods of amplifying target sequences, such as the polymerase chain reaction, can also be used to prepare DNA encoding thymokine proteins. Polymerase chain reaction (PCR) technology is used to amplify such nucleic acid sequences directly from mRNA, from cDNA, and from genomic libraries or cDNA libraries. The isolated sequences encoding thymokine proteins may also be used as templates for PCR amplification.

In PCR techniques, oligonucleotide primers complementary to two 5' regions in the DNA region to be amplified are synthesized. The polymerase chain reaction is then carried out using the two primers. See Innis et al. (eds.) (1990) *PCR Protocols: A Guide to Methods and Applications* Academic Press, San Diego, Calif. Primers can be selected to amplify the entire regions encoding a full-length thymokine protein or to amplify smaller DNA segments as desired. Once such regions are PCR-amplified, they can be sequenced and oligonucleotide probes can be prepared from sequence obtained using standard techniques. These probes can then be used to isolate DNA's encoding thymokine proteins.

Oligonucleotides for use as probes are chemically synthesized according to the solid phase phosphoramidite triester method first described by Beaucage and Carruthers (1983) *Tetrahedron Lett.* 22(20): 1859–1862, or using an automated synthesizer, as described in Needham-VanDevanter et al. (1984) *Nucleic Acids Res.* 12: 6159–6168. Purification of oligonucleotides is performed e.g., by native acrylamide gel electrophoresis or by anion-exchange HPLC as described in Pearson and Regnier (1983) *J. Chrom.* 255: 137–149. The sequence of the synthetic oligonucleotide can be verified using the chemical degradation method of Maxam, A. M. and Gilbert, W. in Grossman, L. and Moldave (eds.) (1980) *Methods in Enzymology* 65: 499–560 Academic Press, New York.

An isolated nucleic acid encoding a mouse thymokine protein was isolated and sequenced. This clone has been designated m3C9 and deposited on Feb. 28, 1994, with the A.T.C.C. under accession number 69574, and its nucleotide sequence and corresponding open reading frame are provided in SEQ ID NO 1 and SEQ ID NO 2. Correspondingly, a human clone was isolated, designated A 10–4 and described in SEQ ID NO 3 and SEQ ID NO 4 and deposited on Apr. 19, 1994, with the A.T.C.C. under accession number 69608.

These thymokines exhibit limited similarity to portions of chemokines. See, e.g., Matsushima and Oppenheim (1989) *Cytokine* 1: 2–13; Oppenheim et al. (1991) *Ann. Rev. Immunol.* 9: 617–648; Schall (1991) *Cytokine* 3: 165–183; and Gronenborn and Clore (1991) *Protein Engineering* 4: 263–269. In particular, mouse lymphotactin shows similarity to the CC class of chemokines in the carboxyl-terminal portion, particularly at the positions corresponding, in the numbering assigned from SEQ ID No. 1, to the ala-val-ile sequence at positions 67–69 through the segment of ile-cys-ala-asp-pro at positions 78–82, the conserved valine at position 87, the hydrophobic residue at position 94, and charged residue at position corresponding to 95. Substantial similarity in the corresponding portion of human lymphotactin also exists, e.g., amino acids of the region of 67–84 of the mouse correspond to residues 61–78 of the human. Thymokines have a longer carboxyl terminal tail than the members of the CC chemokine family. Notably, the spacing of other conserved residues in the CxC and CC families of chemokines are absent in the m3C9 thymokine embodiment. Other features of comparison are apparent between the thymokine and chemokine families. See, e.g., Lodi et al. (1994) *Science* 263: 1762–1766. In particular, β-sheet and α-helix residues are described in Gronenberg et al. (1991) *Protein Engineering* 4: 263–269; and other structural features are defined in Lodi et al (1994) *Science* 263:1762–1767. These secondary and tertiary features assist in defining further the CC and CXC structural features, along with spacing of appropriate cysteine residues between 34 and 40, preferably 36–38, and in specific embodiments, is conserved at 37.

This invention provides isolated DNA or fragments to encode a biologically, active thymokine protein. In addition, this invention provides isolated or recombinant DNA which encodes a biologically active protein or polypeptide which is capable of hybridizing under appropriate conditions, e.g., high stringency, with the DNA sequences described herein. Said biologically active protein or polypeptide can be an intact ligand, or fragment, and have an amino acid sequence as disclosed in SEQ ID NO 2 or SEQ ID NO 4. Preferred embodiments will be full length natural isolates, e.g., about 11,000 to 12,500 daltons in size when unglycosylated, or fragments of at least about 6,000 daltons, more preferably at least about 8,000 daltons. In glycosylated form, the protein may exceed 12,500 daltons. Further, this invention covers the use of isolated or recombinant DNA, or fragments thereof, which encode proteins which are homologous to a thymokine protein or which were isolated using cDNA encoding a thymokine protein as a probe. The isolated DNA can have the respective regulatory sequences in the 5' and 3' flanks, e.g., promoters, enhancers, poly-A addition signals, and others.

IV. Making Thymokines

DNAs which encode a thymokine or fragments thereof can be obtained by chemical synthesis, screening cDNA libraries, or by screening genomic libraries prepared from a wide variety of cell lines or tissue samples.

These DNAs can be expressed in a wide variety of host cells for the synthesis of a full-length protein or fragments which can in turn, for example, be used to generate polyclonal or monoclonal antibodies; for binding studies; for construction and expression of modified molecules; and for structure/function studies. Each thymokine or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, e.g., thymokine, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode a thymokine, or a fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a thymokine protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a thymokine gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function are suitable for use herein. See, e.g., Pouwels et al. (1985 and Supplements) *Cloning Vectors: A Laboratory Manual* Elsevier, N.Y.; and Rodriquez et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, E. coli and its vectors will be used generically to include equivalent vectors used in other prokaryotes. A representative vector for amplifying DNA is pBR322 or its derivatives. Vectors that can be used to express thymokines or thymokine fragments include, but are not limited to, such vectors as those containing the lac promoter (pUC-series); trp promoter (pBR322-trp); lpp promoter (the pIN-series); lambda-pP or pR promoters (pOTS); or hybrid promoters such as ptac (pDR540). See Brosius et al. (1988) "Expression Vectors Employing Lambda-, trp-, lac-, and lpp-derived Promoters", in Rodriguez and Denhardt (eds.) *Vectors: A Survey of Molecular Cloning Vectors and Their Uses* 10: 205–236 Buttersworth, Boston, Mass.

Lower eukaryotes, e.g., yeasts and Dictyostelium, may be transformed with thymokine sequence containing vectors.

For purposes of this invention, the most common lower eukaryotic host is the baker's yeast, Saccharomyces cerevisiae. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active thymokine protein. In principle, any higher eukaryotic tissue culture cell line may be used, e.g., insect baculovirus expression systems, whether from an invertebrate or vertebrate source. However, mammalian cells are preferred to achieve proper processing, both cotranslationally and posttranslationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama et al (1985) *Mol Cell Biol.* 5: 1136–1142; pMC1neo Poly-A, see Thomas et al. (1987) *Cell* 51: 503–512; and a baculovirus vector such as pAC 373 or pAC 610.

Our work indicates that thymokines need not be glycosylated to elicit biological responses in the assays described herein. However, it will often be desirable to express a thymokine polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, the thymokine gene may be co-transformed with one or more genes encoding mammalian or other glycosylating enzymes. It is further understood that over glycosylation may be detrimental to thymokine biological activity, and that one of skill may perform routine testing to optimize the degree of glycosylation which confers optimal biological activity.

A thymokine, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988: 427–454; Tse et al. (1985) *Science* 230: 1003–1008; and Brunner et al. (1991) *J. Cell Biol.* 114: 1275–1283.

Now that thymokines have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; and Bodanszky (1984) *The Principles of Peptide Synthesis* Springer-Verlag, New York, N.Y. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The thymokines of this invention can be obtained in varying degrees of purity depending upon its desired use. Purification can be accomplished by use of known protein purification techniques or by the use of the antibodies or binding partners herein described, e.g., in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the thymokines as a result of DNA techniques, see below.

Multiple cell lines may be screened for one which expresses a thymokine at a high level compared with other cells. Various cell lines, e.g., a mouse thymic stromal cell line TA4, is screened and selected for its favorable handling properties. Natural thymokines can be isolated from natural sources, or by expression from a transformed cell using an appropriate expression vector. Purification of the expressed protein is achieved by standard procedures, or may be combined with engineered means for effective purification at high efficiency from cell lysates or supernatants. FLAG or His$_6$ segments can be used for such purification features.

V. Antibodies

Antibodies can be raised to various thymokines, including individual, allelic, strain, or species variants, and fragments thereof, both in their naturally occurring (full-length) forms and in their recombinant forms. Additionally, antibodies can be raised to thymokines in either their active forms or in their inactive forms. Anti-idiotypic antibodies may also be used.

a. Antibody Production

A number of immunogens may be used to produce antibodies specifically reactive with thymokine proteins. Recombinant protein is the preferred immunogen for the production of monoclonal or polyclonal antibodies. Naturally occurring protein may also be, used either in pure or impure form. Synthetic peptides made using the human or mouse lymphotactin protein sequences described herein may also used as an immunogen for the production of antibodies to thymokines. Recombinant protein can be expressed in eukaryotic or prokaryotic cells as described herein, and purified as described. The product is then injected into an animal capable of producing antibodies. Either monoclonal or polyclonal antibodies may be generated for subsequent use in immunoassays to measure the protein.

Methods of producing polyclonal antibodies are known to those of skill in the art. In brief, an immunogen, preferably a purified protein, is mixed with an adjuvant and animals are immunized with the mixture. The animal's immune response to the immunogen preparation is monitored by taking test bleeds and determining the titer of reactivity to the thymokine protein of interest. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein (1976) *Eur. J. Immunol.* 6: 511–519, incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al (1989) *Science* 246: 1275–1281.

Antibodies, including binding fragments and single chain versions, against predetermined fragments of thymokines can be raised by immunization of animals with conjugates of the fragments with carrier proteins as described above. Monoclonal antibodies are prepared from cells secreting the desired antibody. These antibodies can be screened for binding to normal or defective thymokines, or screened for agonistic or antagonistic activity, e.g., mediated through a receptor. These monoclonal antibodies will usually bind with at least a $K_D$ of about 1 mM, more usually at least about 300 µM, typically at least about 10 µM, more typically at least about 30 µM, preferably at least about 10 µM, and more preferably at least about 3 µM or better.

In some instances, it is desirable to prepare monoclonal antibodies from various mammalian hosts, such as mice, rodents, primates, humans, etc. Description of techniques for preparing such monoclonal antibodies may be found in, e.g., Stites et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256: 495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, Huse et al. (1989) "Generation of a Large Combinatorial Library of the Immunoglobulin Repertoire in Phage Lambda," *Science* 246: 1275–1281; and Ward, et al. (1989) *Nature* 341: 544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Nat'l Acad. Sci. USA* 86: 10029–10033.

The antibodies of this invention can also be used for affinity chromatography in isolating thymokine protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby purified thymokine protein will be released.

The antibodies may also be used to screen expression libraries for particular expression products. Usually the antibodies used in such a procedure will be labeled with a moiety allowing easy detection of presence of antigen by antibody binding.

Antibodies to thymokines may be used for the identification of cell populations expressing thymokines. By assaying the expression products of cells expressing thymokines it is possible to diagnose disease, e.g., immunecompromised conditions.

Antibodies raised against each thymokine will also be useful to raise anti-idiotypic antibodies. These will be useful in detecting or diagnosing various immunological conditions related to expression of the respective antigens.

b. Immunoassays

A particular protein can be measured by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; and Harlow and Lane *Antibodies, A Laboratory Manual*, supra, each of which is incorporated herein by reference. See also Chan (ed.) (1987) *Immunoassay: A Practical Guide* Academic Press, Orlando, Fla.; Price and Newman (eds.) (199 1) *Principles and Practice of Immunoassays* Stockton Press, N.Y.; and Ngo (ed.) (1988) *Non-isotopic Immunoassays* Plenum Press, N.Y.

Immunoassays for measurement of thymokine proteins can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with thymokine proteins produced as described above. The concentration of labeled analyte bound to the capture agent is inversely proportional to the amount of free analyte present in the sample.

In a competitive binding immunoassay, the thymokine protein present in the sample competes with labelled protein for binding to a specific binding agent, for example, an antibody specifically reactive with the thymokine protein. The binding agent may be bound to a solid surface to effect separation of bound labelled protein from the unbound labelled protein. Alternately, the competitive binding assay may be conducted in liquid phase and any of a variety of techniques known in the art may be used to separate the bound labelled protein from the unbound labelled protein. Following separation, the amount of bound labeled protein is determined. The amount of protein present in the sample is inversely proportional to the amount of labelled protein binding.

Alternatively, a homogenous immunoassay may be performed in which a separation step is not needed. In these immunoassays, the label on the protein is altered by the binding of the protein to its specific binding agent. This alteration in the labelled protein results in a decrease or increase in the signal emitted by label, so that measurement of the label at the end of the immunoassay allows for detection or quantitation of the protein.

Thymokine proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labelled. After binding at both sites on the protein has occurred, the unbound labelled binding agent is removed and the amount of labelled binding agent bound to the solid phase is measured. The amount of labelled binding agent bound is directly proportional to the amount of protein in the sample.

Western blot analysis can be used to determine the presence of thymokine proteins in a sample. Electrophoresis is carried out, for example, on a tissue sample suspected of containing the protein. Following electrophoresis to separate the proteins, and transfer of the proteins to a suitable solid support such as a nitrocellulose filter, the solid support is incubated with an antibody reactive with the protein. This antibody may be labelled, or alternatively may be it may be detected by subsequent incubation with a second labelled antibody that binds the primary antibody.

The immunoassay formats described above employ labelled assay components. The label can be in a variety of forms. The label may be coupled directly or indirectly to the desired component of the assay according to methods well known in the art. A wide variety of labels may be used. The component may be labelled by any one of several methods. Traditionally a radioactive label incorporating $^3$H, $^{125}$I, $^{35}$S, $^{14}$C, or $^{32}$P was used. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation. For a review of various labelling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

In brief, immunoassays to measure antisera reactive with thymokine proteins can be either competitive or noncompetitive binding assays. In competitive binding assays, the sample analyte competes with a labeled analyte for specific binding sites on a capture agent bound to a solid surface. Preferably the capture agent is a purified recombinant thymokine protein produced as described above. Other sources of thymokine proteins, including isolated or partially purified naturally occurring protein, may also be used. Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means. A number of combinations of capture agent and labelled binding agent can be used. A variety of different immunoassay formats, separation techniques and labels can be also be used similar to those described above for the measurement of thymokine proteins.

VI. Purified Thymokines

A mouse thymokine amino acid sequence is provided in SEQ ID NO 2. Human amino acid and nucleotide sequences are provided in SEQ ID NO 3 and SEQ ID NO 4. The peptide sequences allow preparation of peptides to generate antibodies to recognize such segments, and allow preparation of oligonucleotides which encode such sequences. Since thymokines appear to be secreted proteins, they will have an N-terminal signal sequence, which is removed upon processing and secretion, and the putative cleavage site is between amino acids 20 (glu) and 21 (gly) in SEQ ID NO 2. Analysis of the structural features in comparison with the most closely related reported sequences has revealed similarities with other cytokines, particularly the class of proteins known as chemokines. Within the chemokines are two subgroups, the CC and CxC subgroups. The thymokine family shares various features with each of these groups, but its combination of features is distinctive and defines a new family of related chemokines.

VII. Physical Variants

This invention also encompasses proteins or peptides having substantial amino acid sequence similarity with an amino acid sequence of a thymokine. Natural variants include individual, allelic, strain, or species variants.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

Homologous amino acid sequences include natural allelic and interspecies variations in each respective protein sequence. Typical homologous proteins or peptides will have from 50–100% similarity (if gaps can be introduced), to 75–100% similarity (if conservative substitutions are included) with the amino acid sequence of the thymokine. Similarity measures will be at least about 50%, generally at least 60%, more generally at least 65%, usually at least 70%, more usually at least 75%, preferably at least 80%, and more preferably at least 80%, and in particularly preferred embodiments, at least 85% or more. See also Needleham et al. (1970) *J. Mol. Biol.* 48: 443–453; Sankoff et al (1983) *Time Warps, String Edits, and Macromolecules: The Theory and Practice of Sequence Comparison* Chapter One, Addison-Wesley, Reading, Mass.; and software packages from IntelliGenetics, Mountain View, Calif.; and the University of Wisconsin Genetics Computer Group, Madison, Wis.

Nucleic acids encoding mammalian thymokine proteins will typically hybridize to the nucleic acid sequence of SEQ ID NO 1 or SEQ ID NO 3 under stringent conditions. For example, nucleic acids encoding mouse lymphotactin proteins will hybridize to the nucleic acid of SEQ ID NO 1 under stringent hybridization conditions. Generally, stringent conditions are selected to be about 10° C. lower than the thermal melting point (Tm) for the sequence being hybridized to at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 200 mM NaCl at 42° C.

An isolated thymokine DNA can be readily modified by nucleotide substitutions, nucleotide deletions, nucleotide insertions, and inversions of nucleotide stretches. These modifications result in novel DNA sequences which encode thymokine antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant thymokine derivatives include predetermined or site-specific mutations of the respective protein or its fragments.

"Mutant thymokine" encompasses a polypeptide otherwise falling within the homology definition of the mouse thymokine as set forth above, but having an amino acid sequence which differs from that of a thymokine as found in nature, whether by way of deletion, substitution, or insertion. In particular, "site specific mutant thymokine" generally includes proteins having significant similarity with a protein having a sequence of SEQ ID NO 2 or SEQ ID NO 4, and as sharing various biological activities, e.g., antigenic or immunogenic, with those sequences, and in preferred embodiments contain most or all of the disclosed sequence. Similar concepts apply to different thymokine proteins, particularly those found in various warm blooded animals, e.g., mammals and birds. As stated before, it is emphasized that descriptions are generally meant to encompass other thymokine proteins, not limited to the mouse or human embodiments specifically discussed.

Although site specific mutation sites are predetermined, mutants need not be site specific. Thymokine mutagenesis can be conducted by making amino acid insertions or deletions. Substitutions, deletions, insertions, or any combinations may be generated to arrive at a final construct. Insertions include amino- or carboxyl- terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook et al (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a thymokine polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, protein-binding or other segments may be "swapped" between different new fusion polypeptides or fragments. See, e.g., Cunningham et al. (1989) *Science* 243: 1330–1336; and O'Dowd et al. (1988) *J. Biol Chem.* 263: 15985–15992. Thus, new chimeric polypeptides exhibiting new combinations of specificities will result from the functional linkage of protein-binding specificities and other functional domains.

VIII. Binding Agent:Thymokine Protein Complexes

A thymokine protein that specifically binds to or that is specifically immunoreactive with an antibody generated against a defined immunogen, such as an immunogen consisting of the amino acid sequence of SEQ ID NO 2 or SEQ ID NO 4, is determined in an immunoassay. The immunoassay uses a polyclonal antiserum which was raised to the protein of SEQ ID NO 2 or SEQ ID NO 4. This antiserum is selected to have low crossreactivity against other chemokines and any such crossreactivity is removed by immunoabsorbtion prior to use in the immunoassay.

In order to produce antisera for use in an immunoassay, the protein of SEQ ID NO 2 or SEQ ID NO 4 is isolated as described herein. For example, recombinant protein may be produced in a mammalian cell line. An inbred strain of mice such as balb/c is immunized with the protein of SEQ ID NO 2 or SEQ ID NO 4 using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against C-C and CXC chemokines, using a competitive binding immunoassay such as the one described in Harlow and Lane, supra, at-pages 570–573. Preferably two chemokines are used in this determination in conjunction with either human lymphotactin or mouse lymphotactin. In conjunction with mouse lymphotactin, the monocyte chemotactic protein-1 (MCP-1) and macrophage inflammatory protein-1α (Mip-1α) are used to identify antibodies which are specifically bound by a thymokine. In conjunction with human lymphotactin, the monocyte chemotactic protein-2 (MCP-2) and Mip-1α are used to identify antibodies which are specifically bound by a thymokine. These chemokines can be produced as recombinant proteins and isolated using standard molecular biology and protein chemistry techniques as described herein.

Immunoassays in the competitive binding format can be used for the crossreactivity determinations. For example, the protein of SEQ ID NO 2 or SEQ ID NO 4 can be immobilized to a solid support. Proteins added to the assay compete with the binding of the antisera to the immobilized antigen. The ability of the above proteins to compete with the binding of the antisera to the immobilized protein is compared to the protein of SEQ ID NO 2, or SEQ ID NO 4. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (e.g., the thymokine protein of SEQ ID NO 2 or SEQ ID NO 4). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO 2 that is required, then the second protein is said to specifically bind to an antibody generated to the immunogen.

It is understood that thymokine proteins are a family of homologous proteins that comprise two or more genes. For a particular gene product, such as the human lymphotactin protein, the term refers not only to the amino acid sequences disclosed herein, but also to other proteins that are allelic, non-allelic or species variants. It also understood that the term "human lymphotactin" or "mouse lymphotactin" includes nonnatural mutations introduced by deliberate mutation using conventional recombinant technology such as single site mutation, or by excising short sections of DNA encoding lymphotactin proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring lymphotactin protein, for example, the human lymphotactin protein shown in SEQ ID NO 4. The biological properties of the altered proteins can be determined by expressing the protein in an appropriate cell line and measuring the chemotactic effect upon lymphocytes as described herein. Particular protein modifications considered minor would include conservative substitution of amino acids with similar chemical properties, as described above for the thymokine family as a whole. By aligning a protein optimally with the protein of SEQ ID NO 2 and SEQ ID NO 4 and by using the conventional immunoassays described herein to determine immunoidentity, or by using lymphocyte chemotaxis assays, one can determine the protein compositions of the invention.

IX. Functional Variants

The blocking of physiological response to thymokines may result from the inhibition of binding of the protein to its receptor, e.g., through competitive inhibition. Thus, in vitro assays of the present invention will often use isolated protein, membranes from cells expressing a recombinant membrane associated thymokine, soluble fragments comprising receptor binding segments of these proteins, or fragments attached to solid phase substrates. These assays will also allow for the diagnostic determination of the effects of either binding segment mutations and modifications, or protein mutations and modifications, e.g., protein analogues. This invention also contemplates the use of competitive drug screening assays, e.g., where neutralizing antibodies to antigen or receptor fragments compete with a test compound for binding to the protein. In this manner, the antibodies can be used to detect the presence of any polypeptide which shares one or more antigenic binding sites of the protein and can also be used to occupy binding sites on the protein that might otherwise interact with a receptor.

"Derivatives" of thymokine antigens include amino acid sequence mutants, glycosylation variants, and covalent or aggregate conjugates with other chemical moieties. Covalent derivatives can be prepared by linkage of functionalities to groups which are found in thymokine amino acid side chains or at the N- or C- termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

A major group of derivatives are covalent conjugates of the thymokine or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between thymokines and other homologous or heterologous proteins are also provided.

Many growth factors and cytokines are homodimeric entities, and a repeat construct may have various advantages, including lessened susceptibility to proteolytic degradation. Moreover, many receptors require dimerization to transduce a signal, and various dimeric proteins or domain repeats can be desirable. Heterologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski et al. (1988) Science 241: 812–816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of thymokines other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a thymokine antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-thymokine antibodies or its receptor. The thymokines can also be labeled with a detectable group, for example radioiodinated by the chloramine T procedure, covalently bound to rare earth chelates, or conjugated to another fluorescent moiety for use in diagnostic assays. Purification of thymokines may be effected by immobilized antibodies or receptor.

Isolated thymokine genes will allow transformation of cells lacking expression of a corresponding thymokines, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of thymokine receptor proteins. Subcellular fragments, e.g., cytoplasts or membrane fragments, can be isolated and used.

X. Uses

The present invention provides reagents which will find use in diagnostic applications as described elsewhere herein, e.g., in the general description for developmental abnormalities, or below in the description of kits for diagnosis.

Thymokine nucleotides, e.g., human or mouse lymphotactin DNA or RNA may be used as a component in a forensic assay. For instance, the nucleotide sequences provided may be labeled using, e.g., $^{32}P$ or biotin and used to probe standard restriction fragment polymorphism blots, providing a measurable character to aid in distinguishing between individuals. Such probes may be used in well-known forensic techniques such as genetic fingerprinting. In addition, nucleotide probes made from thymokine sequences may be used in in situ assays to detect chromosomal abnormalities. For instance, rearrangements in mouse chromosome 1 may be detected via well-known in situ techniques, using thymokine probes in conjunction with other known chromosome 1 markers.

Thymokine proteins may be used as chemotactic agents for separating lymphocyte cells such as pro-T cells from a general population of cells, in vitro or in vivo. For instance, lymphocyte subpopulations such as pro-T cells ($CD44^+$ $CD25^+CD3^-CD4^-CD8^-$ cells) may be separated from neutrophils and monocytes based upon the chemotactic properties of thymokines such as mouse or human lymphotactin. The relative proportion of such cells in a population of cell types may be used as a diagnostic indicator of disease states which involve e.g., immune-system disorders and genetic defects. In addition, the isolated cells, may be used as therapeutic agents, or as targets for gene-therapy. Note in this context that pluripotent cells such as pro-T cells are particularly desirable targets for gene therapy.

Antibodies and other binding agents directed towards thymokine proteins or nucleic acids may be used to purify the corresponding thymokine molecule. As described in the Examples below, antibody purification of thymokine components is both possible and practicable. Antibodies and other binding agents may also be used in a diagnostic fashion to determine whether thymokine components are present in a tissue sample or cell population using well-known techniques described herein. The ability to attach a binding agent to a thymokine provides a means to diagnose disorders associated with thymokine misregulation. Antibodies and other thymokine binding agents may also be useful as histological markers. As described in the examples below, thymokine expression is limited to specific tissue types. By directing a probe, such as an antibody or nucleic acid to a thymokine it is possible to use the probe to distinguish tissue and cell types in situ or in vitro.

This invention also provides reagents with significant therapeutic value. The thymokines (naturally occurring or recombinant), fragments thereof, and antibodies thereto, along with compounds identified as having binding affinity to a thymokine, are useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a thymokine is a target for an agonist or antagonist of the protein. The proteins likely play a role in regulation or development of hematopoietic cells, e.g., lymphoid cells, which affect immunological responses, e.g., autoimmune disorders.

Other abnormal developmental conditions are known in cell types shown to possess thymokine mRNA by northern blot analysis. See Berkow (ed.) The Merck Manual of Diagnosis and Therapy, Merck & Co., Rahway, N.J.; and Thorn et al Harrison's Principles of Internal Medicine, McGraw-Hill, N.Y. Developmental or functional abnormalities, e.g., of the immune system, cause significant medical abnormalities and conditions which may be susceptible to prevention or treatment using compositions provided herein.

Recombinant thymokine or thymokine antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to thymokines, including isolation of associated components. Subsequent biological assays can then be utilized to determine if the compound has intrinsic stimulating activity and is therefore a blocker or antagonist in that it blocks the activity of the protein. Likewise, a compound having intrinsic stimulating activity can activate the receptor and is thus an agonist in that it simulates the activity of a thymokine. This invention further contemplates the therapeutic use of antibodies to thymokines as antagonists. This approach should be particularly useful with other thymokine species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 μM concentrations, usually less than about 100 nM, preferably less than about 10 μPM (picomolar), and most preferably less than about 1 fM (femtomolar), with an appropriate carrier. Slow release formulations, or a slow release apparatus will often be utilized for continuous administration.

Thymokines, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman et al (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, P.a.; Avis et al (eds.) (1993) *Pharmaceutical Dosage Forms: Parenteral Medications Dekker*, N.Y.; Lieberman et al. (eds.) (1990) *Pharmaceutical Dosgae Forms: Tablets Dekker*, N.Y.; and Lieberman et al (eds.) (1990) *Pharmaceutical Dosage Forms: Disperse Systems* Dekker, N.Y. The therapy of this invention may be combined with or used in association with other chemotherapeutic or chemopreventive agents.

Both the naturally occurring and the recombinant form of the thymokines of this invention are particularly useful in kits and assay methods which are capable of screening compounds for binding activity to the proteins. Several methods of automating assays have been developed in recent years so as to permit screening of tens of thousands of compounds in a short period. See, e.g., Fodor et al. (1991) *Science* 251: 767–773, and other descriptions of chemical diversity libraries, which describe means for testing of binding affinity by a plurality of compounds. The development of suitable assays can be greatly facilitated by the availability of large amounts of purified, soluble thymokine as provided by this invention.

For example, antagonists can normally be found once the protein has been structurally defined. Testing of potential protein analogues is now possible upon the development of highly automated assay methods using a purified receptor. In particular, new agonists and antagonists will be discovered by using screening techniques described herein. Of particular importance are compounds found to have a combined binding affinity for multiple thymokine receptors, e.g., compounds which can serve as antagonists for species variants of a thymokine.

This invention is particularly useful for screening compounds by using recombinant receptor in a variety of drug screening techniques. The advantages of using a recombinant protein in screening for specific ligands include: (a) improved renewable source of the thymokine receptor from a specific source; (b) potentially greater number of ligands per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing a thymokine receptor. Cells may be isolated which express a receptor in isolation from any others. Such cells, either in viable or fixed form, can be used for standard ligand/receptor binding assays. See also, Parce et al. (1989) *Science* 246: 243–247; and Owicki et al. (1990) *Proc. Nat'l Acad. Sci. USA* 87: 4007–4011, which describe sensitive methods to detect cellular responses. Competitive assays are particularly useful, where the cells (source of thymokine) are contacted and incubated with a labeled receptor or antibody having known binding affinity to the ligand, such as $^{125}$I-antibody, and a test sample whose binding affinity to the binding composition is being measured. The bound and free labeled binding compositions are then separated to assess the degree of ligand binding. The amount of test compound bound is inversely proportional to the amount of labeled receptor binding to the known source. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on thymokine mediated functions, e.g., second messenger levels, i.e., $Ca^{++}$; cell proliferation; inositol phosphate pcol changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of a thymokine. These cells are stably transformed with DNA vectors directing the expression of a thymokine, e.g., an engineered membrane bound form. Essentially, the membranes would be prepared from the cells and used in a receptor/ligand binding assay such as the competitive assay set forth above.

Still another approach is to use solubilized, unpurified or solubilized, purified thymokine from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to a thymokine receptor and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor et al., supra. Then all the pins are reacted with solubilized, unpurified or solubilized, purified thymokine receptor, and washed. The next step involves detecting bound thymokine receptor.

Rational drug design may also be based upon structural studies of the molecular shapes of the thymokine and other effectors or analogues. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, N.Y.

A purified thymokine can be coated directly onto plates for use in the aforementioned drug screening techniques. However, non-neutralizing antibodies to these ligands can be used as capture antibodies to immobilize the respective ligand on the solid phase.

XI. Kits

This invention also contemplates use of thymokine proteins, fragments thereof, peptides, and their fusion products in a variety of diagnostic kits and methods for detecting the presence of thymokine or a thymokine receptor. Typically the kit will have a compartment containing either a defined thymokine peptide or gene segment or a reagent which recognizes one or the other, e.g., receptor fragments or antibodies.

A kit for determining the binding affinity of a test compound to a thymokine would typically comprise a test compound; a labeled compound, for example a receptor or antibody having known binding affinity for the thymokine; a source of thymokine (naturally occurring or recombinant); and a means for separating bound from free labeled compound, such as a solid phase for immobilizing the thymokine. Once compounds are screened, those having suitable binding affinity to the thymokine can be evaluated in suitable biological assays, as are well known in the art, to determine whether they act as agonists or antagonists to the receptor. The availability of recombinant thymokine polypeptides also provide well defined standards for calibrating such assays.

A preferred kit for determining the concentration of, for example, a thymokine in a sample would typically comprise a labeled compound, e.g., receptor or antibody, having known binding affinity for the thymokine, a source of thymokine (naturally occurring or recombinant) and a means for separating the bound from free labeled compound, for example, a solid phase for immobilizing the thymokine. Compartments containing reagents, and instructions, will normally be provided.

Antibodies, including antigen binding fragments, specific for the thymokine or ligand fragments are useful in diagnostic applications to detect the presence of elevated levels of thymokine and/or its fragments. Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and antigen-thymokine complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a thymokine or to a particular fragment thereof. Similar assays have also been extensively discussed in the literature. See, e.g., Harlow and Lane (1988) *Antibodies: A Laboratory Manual,* CSH Press, N.Y.; Chan (ed.) (1987) *Immunoassay: A Practical Guide* Academic Press, Orlando, Fla.; Price and Newman (eds.) (1991) *Principles and Practice of Immunoassay* Stockton Press, N.Y.; and Ngo (ed.) (1988) *Nonisotopic Immunoassay* Plenum Press, N.Y.

Anti-idiotypic antibodies may have similar use to diagnose presence of antibodies against a thymokine, as such may be diagnostic of various abnormal states. For example, overproduction of thymokine may result in production of various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled thymokine is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or noncovalently joining a moiety which directly or indirectly provides a detectable signal. In any of these assays, the protein, test compound, thymokine, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free ligand, or alternatively the bound from the free test compound. The thymokine can be immobilized on various matrices followed by washing. Suitable matrices include plastic such as an ELISA plate, filters, and beads. Methods of immobilizing the thymokine to a matrix include, without limitation, direct adhesion to plastic, use of a capture antibody, chemical coupling, and biotin-avidin. The last step in this approach involves the precipitation of ligand/receptor or ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle et al. (1984) *Clin. Chem.* 30: 1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a thymokine. These sequences can be used as probes for detecting levels of the thymokine message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet et al (1989) *Progress in Growth Factor Res.* 1: 89–97.

XII. Receptor Isolation

Having isolated a binding partner of a specific interaction, methods exist for isolating the counter-partner. See, Gearing et al. (1989) *EMBO J.* 8: 3667–3676. For example, means to label a thymokine without interfering with the binding to its receptor can be determined. For example, an affinity label can be fused to either the amino- or carboxyl-terminus of the ligand. An expression library can be screened for specific binding of the thymokine, e.g., by cell sorting, or other screening to detect subpopulations which express such a binding component. See, e.g., Ho et al. (1993) *Proc. Nat'l Acad. Sci. USA* 90: 11267–11271. Alternatively, a panning method may be used. See, e.g., Seed and Aruffo (1987) *Proc. Nat'l Acad. Sci. USA* 84: 3365–3369.

Protein cross-linking techniques with label can be applied to isolate binding partners of a thymokine. This would allow identification of proteins which specifically interact with a thymokine, e.g., in a ligand-receptor like manner.

The broad scope of this invention is best understood with reference to the following examples, which are not intended to limit the invention to specific embodiments.

EXAMPLES

General Methods

Many of the standard methods below are described or referenced, e.g., in Maniatis et al. (1982) *Molecular Cloning, A Laboratory Manual* Cold Spring Harbor Laboratory, Cold Spring Harbor Press, N.Y.; Sambrook et al (1989) *Molecular Cloning: A Laboratory Manual* (2d ed.) Vols. 1–3, CSH Press, N.Y.; Ausubel et al., *Biology* Greene Publishing Associates, Brooklyn, N.Y.; or Ausubel et al. (1987 and Supplements) *Current Protocols in Molecular Biology* Wiley/Greene, N.Y.; Innis et al. (eds.) (1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel et al (1987 and periodic supplements); Deutscher (1990) "Guide to Protein Purification," *Methods in Enzymology* vol. 182, and other volumes in this series; and manufacturer's literature on use of protein purification products, e.g., Pharmacia, Piscataway, N.J., or Bio-Rad, Richmond, Calif., Combination with recombinant techniques allow fusion to appropriate segments, e.g., to a FLAG sequence or an equivalent which can be fused via a protease-removable sequence. See, e.g., Hochuli (1989) *Chemische Industrie* 12: 69–70;

Hochuli (1990) "Purification of Recombinant Proteins with Metal Chelate Absorbent" in Setlow (ed.) *Genetic Engineering, Principle and Methods* 12: 87–20 98, Plenum Press, N.Y.; and Crowe et al. (1992) *QIAexpress: The High Level Expression & Protein Purification System* QIAGEN, Inc., Chatsworth, Calif.

FACS analyses are described in Melamed et al. (1990) *Flow Cytometry and Sorting* Wiley-Liss, Inc., New York, N.Y.; Shapiro (1988) *Practical Flow Cytometry* Liss, New York, N.Y.; and Robinson et al. (1993) *Handbook of Flow Cytometry Methods* Wiley-Liss, New York, N.Y.

Example 1
Isolation of a Mouse Thymokine Gene by Subtractive Hybridization from Stimulated $CD44^+CD25^+CD3^-CD4^-CD8$ Cells The screening approach used to isolate mouse lymphotactin is termed differential screening, or differential screening by subtractive hybridization. In general, this procedure utilizes RNA probes generated from two categories of cDNA libraries. The first category contains probes from cDNA libraries generated from cell types that are not to be characterized. The cDNA libraries employed in this screening were generated as described below from D10.G4.1, HC7, and HT-2 T cell lines in the PCDNA I or PCDNA II plasmid (Invitrogen) containing an SP6 and T7 promoter. The second category contains probes from the cDNA library to be characterized. The cDNA library employed in this screening was prepared from the Pro T cells as described below.

Pro T cells ($CD44^+CD25^+CD3^-CD4^-CD8^-$) from Balb/c mice were prepared for sorting on a FACS by labeling with appropriate antibodies using standard techniques (Godfrey et al (1993) *J. Immunol.* 150: 4244–52). Sorted Pro T cells were activated for 6 hours as described below, and cultured in IL-7, stem cell factor, and IL-2 for 12 days to expand. Cells were then reactivated for 6 hours prior to harvesting, and stored at –70° C. In order to assess the quality of the second activation an aliquot of cells was transferred to fresh complete media after the 6 hour activation and cultured overnight. Supernatant from these cultures was assayed on the IL-2 dependent cell line HT-2. Only cultures which demonstrated high titers of IL-2 after activation were used in generating the cDNA libraries. In this manner cells were accumulated and later pooled to isolate mRNA.

The D10.G4.1 T cell line which demonstrates a Th2 phenotype, the HC7 T-cell line which demonstrates a Th1 phenotype, and the HT-2 T cell line which was used as a "housekeeping" gene T cell line were employed to make cDNA libraries for screening the Pro T cell cDNA library. The D10.G4.1 line was expanded in culture and activated on anti-CD3 (Pharmingen) coated culture plates (10 µg/ml) for 6 hours before harvesting and storing at –70° C. These cells were assayed for quality of activation as described above. The HT-2 cells were expanded in culture media containing IL-2 (490 U/ml), washed in PBS, and stored at –70° C.

mRNA was prepared by the FastTrack kit (Invitrogen) from which cDNA was generated using SuperScript Plasmid System for cDNA synthesis from GIBCO-BRL (Gathersburg, Md.) essentially as described by the manufacturer. One modification to the procedure was the substitution of BstXI adapters (Invitrogen) for the Sal 1 adapters provided with the kit. The resultant cDNA from these cells was used to generate libraries in the plasmid PCDNA II (Invitrogen). The cDNA was cloned into the BstXI/NotI site in the polylinker and was used to transform the DH10B strain of *E.coli*. Plasmid was isolated and purified with the Qiagen system (Chatsworth, Calif.) which was used to generate RNA probes from the SP6 promoter. A second cDNA library from the Pro T cells was generated in the BstXI/NotI polylinker of the plasmid pJFE14 SR alpha (J. F. Elliott et al. (1990) *Proc. Natl. Acad. Sci. USA* 87: 6363–7). This library was used to transform DH10B and the bacteria was plated on agarose, transferred to nylon membranes in triplicate, and screened with RNA probes from the other libraries. Chemiluminescent detection of hybridization employed the Genius system (Boehringer-Mannheim).

RNA probes were labeled using the Genius System (Boehringer-Mannheim) as described by the manufacturer. However, both the SP6 and T7 RNA polymerase used were obtained from Promega (Madison, Wis. Both the HT-2 probe and Pro T cell probe were each used at 10 ng/ml, the HC7 and D10.G4.1 probes were each used at 5 ng/ml and were combined into one probe mix. The filter lifts of the Pro T cell pJFE cDNA library were pre-hybridized at 42° C. for 3–6 hours in Church's buffer (50% formamide, 6×SSPE, 50 mM $NaHPO_4$ pH 7.2, 7% SDS, 0.1 % N-Lauryl sarcosine, 2% Boehringer-Mannheim blocking reagent). Filters were probed overnight in the same buffer containing the appropriate probes. Specifically, each filter from the set of triplicate filters was probed with either HT-2 RNA probes, Pro T cell RNA probes, or pooled HC7+D10.G4.1 RNA probes. The filters were washed as described by the Genius System. The colonies that hybridized with the $CD44^+CD25^+TN$ probe but not the HT-2; or D10.G4.1+HC7 probes were selected as unique to the $CD44^+CD25^+TN$ cDNA library. The clones were sequenced and compared to a series of sequence data banks to determine if homology existed between previously reported clones. The clone m3C9 was demonstrated to be previously unreported, and was independently isolated out of the subtraction cloning method described above.

Example 2
Isolation of Mouse Lymphotactin by Subtractive Hybridization from Stimulated $\alpha\beta TcR^+CD4^-CD8^-$ cells.

Antibodies and Flow-Cytometric Sorting $\alpha\beta TcR^+CD4^-CD8^-$ (DN) thymocytes were sorted using CD4/CD8-PE and $\alpha\beta TcR$-FITC mAbs (PharMingen, San Diego, Calif.). See Zlotnik et al (1992) *J. Immunol.* 4: 1211–1215. The sorted cells (approximately $5 \times 10^5$) were stimulated on solid-phase anti-CD3 for 24 h and were then expanded and cultured in IL-2 (500 U/ml) and IL-7 (100 U/ml) for one week (to approximately $1 \times 10^8$ cells). Cells were either harvested after one week in culture or stimulated again for 6 h on anti-CD3 and then harvested.

Construction of Directional cDNA Libraries

Poly (A)+RNA from anti-CD3 stimulated $\alpha\beta DN$ thymocytes or unstimulated $\alpha\beta DN$ thymocytes was used to synthesize first strand cDNA by using NotI/Oligo-dT primer (Gibco-BRL, Gaithersburg, Md.). Double-stranded cDNA was synthesized, ligated with BstXI adaptors, digested with NotI, size fractionated for >0.5 kilobase pairs (kb) and ligated into the NotI/BstXI sites of pJFE-14, a derivative of the pCDSRa vector. See Takebe et al. *Mol Cell Biol.* 8: 466–472. Electro-competent *E. coli* DH 10a cells (Gibco-BRL) were used for transformation. Total number of independent clones of the cDNA libraries were $1.2 \times 10^6$ for stimulated $\alpha\beta DN$ and $8 \times 10^5$ for unstimulated $\alpha\beta DN$ thymocytes, respectively.

PCR-based Library Subtraction

The PCR-based subtraction system developed by Wang and Brown (1991) *Proc. Natl. Acad. Sci. USA* 88: 11505–11509, was modified to apply to plasmid cDNA libraries. A cDNA library specific for activated $\alpha\beta DN$ thymocytes was generated using 100 mg of the unstimulated αβDN cDNA library DNA digested with XbaI, NotI, and ScaI as driver DNA and 5 mg of the stimulated αβDN cDNA library DNA as tracer DNA. Following restriction digestion, the driver DNA was treated with DNA polymerase Klenow fragment to fill-in the restriction sites. After ethanol precipitation, the DNA was dissolved in 100 ml of water, heat-denatured and mixed with 100 ml (100 mg) of Photoprobe biotin (Vector Laboratories, Burlingame, Calif.). The driver DNA was then irradiated with a 270-W sunlamp on ice for 20 min. 50 ml more Photoprobe biotin was added and the biotinylation reaction was repeated. After butanol extraction, the photobiotinylated DNA (driver-U) was ethanol-precipitated and dissolved in 30 ml of 10 mM Tris-HCl and 1 mM EDTA, pH 8 (TE). As tracer DNA, 5 mg of stimulated αβDN cDNA was digested with XbaI and NotI; ethanol precipitated; and dissolved in 4 ml of TE (tracer-S). Tracer-S was mixed with 15 ml of driver-U, 1 ml (10 mg) of *E. coli* tRNA (Sigma, St. Louis, Mo.), and 20 ml of 2×hybridization buffer (1.5M NaCl, 10 mM EDTA, 50 mM HEPES, pH 7.5, 0.2% SDS), overlaid with mineral oil, and heat-denatured. The sample tube was immediately transferred into a 68° C. water bath and incubated for 20 h. The reaction mixture was then subjected to streptavidin treatment followed by phenol/chloroform extraction. Subtracted DNA was precipitated, dissolved in 12 ml of TE, mixed with 8 ml of driver-U and 20 ml of 2×hybridization buffer, and then incubated at 68° C. for 2 h. After streptavidin treatment, the remaining DNA was ligated with 250 ng of a purified XbaI/NotI fragment of pJFE-14 and then transformed into electro-competent *E. coli* cells to generate the activation specific αβDN subtracted library (S1). 100 independent clones were randomly picked and screened by hybridization using a cocktail of known cytokine cDNA's. Plasmid DNA's were prepared from clones that did not hybridize to the cytokine probes. These clones were grouped by insert size and further characterized by DNA sequencing. Clones corresponding to the m3C9 clone described above were isolated.

Example 3
Mouse Lymphotactin Expression.

Poly(A)+RNA was isolated from sorted cell populations using the FastTrack mRNA kit (Invitrogen, San Diego, Calif.). Samples were electrophoresed in a 1 % agarose gel containing formaldehyde and transferred to a GeneScreen membrane (NEN Research Products, Boston, Maas.). Hybridization was performed at 65° C. in 0.5M NaHPO$_4$ pH 7.2, 7% SDS, 1mM EDTA, and 1% BSA (fraction V) with $^{32}$P-dCTP labeled Lymphotactin cDNA at $10^7$ cpm/ml. After hybridization filters were washed three times at 50° C. in 0.2×SSC, 0.1 % SDS, and exposed to film for 24 hrs. In comparison with unactivated cells, phorbol ester activated CD8+thymocyte and splenocyte cells, and Pro T cells had high levels of expression. CD4+thymocyte and splenocyte cells,and DP thymocyte cells showed no increase in expression upon activation.

Lymphotactin is abundant in the Pro T cell cDNA library, at a frequency of 1 in 125 clones. Lymphotactin was also isolated from a cDNA library generated from αβTCR4+CD4−CD8−thymocytes (Zlotnik et al. (1992) *J. Immunol.* 149: 1211–5). RNA blot analysis of T cell subsets confirmed that Lymphotactin was present in activated but not freshly isolated Pro T cells.

A high level of expression of Lymphotactin was detected in both activated thymic CD8+CD3+cells and activated CD8+CD3+T cells derived from the spleen. A low level of expression in activated mature CD4+thymocytes was detected. This weak hybridization signal may be due to the small sub population of CD4+NK1.1+cells (Arase et al. (1992) *Proc. Natl. Acad. Sci. U.S.A.* 89: 6506–10). There was no detectable expression of Lymphotactin in activated CD4+ CD8+thymocytes. Furthermore, hybridization to a mouse multiple tissue RNA blot failed to detect Lymphotactin in heart, brain, spleen, lung, liver, kidney, testis, or skeletal muscle.

Example 4
in vivo and in vitro Pro T-cell cytokine profiles

We have previously characterized Pro T cells, an immature thymocyte subset that is likely to be the final differentiation stage prior to the onset of T cell receptor β chain gene rearrangement (Godfrey et al. (1993) *Immunol. Today* 14: 547–53;

Godfrey et al. (1994) *J. Immunol.* 152: 4783–92). Pro T cells are able to produce high titers of IL-2, TNF-α, and TFN-γ, when activated in vitro with phorbol ester (PMA), calcium ionophore (A23187), and IL-1. In this example we describe in vivo and in vitro cytokine producing profiles of the Pro T cells. A cDNA library generated from activated Pro T cells was screened in to identify novel cytokines.

In order to characterize the cytokine producing potential of Pro T cells both in vitro activated and freshly sorted Pro T cells were analyzed by PCR. Cells were activated 6 hours with calcium ionophore A23187 (Calbiochem, San Diego Calif.) resuspended to 1 mM DMSO and used at 0.35 µM final concentration Phorbol-12-Myristate-13-Acetate (Calbiochem) resuspended to 1 mg/ml in ethanol and used at 10 ng/ml), and IL-1 (Genzyme, Cambridge Mass.) 20 U/ml). Total RNA was isolated from cell pellets with RNAzol (Tel-Test, Inc., Friendswood, Tex.). cDNA was generated from total RNA by poly dT primed reverse transcription. cDNA was used for PCR amplification. For PCR, 5 µl of cDNA directly from the reverse transcription reaction was amplified. To each reaction a 45 µl mix of the following was added: 5 µl 10×AmpliTaq PCR Buffer (Perkin-Elmer Cetus), 1 µl 10 mM dNTP's, 37 µl sterile water, 0.2 µl AmpliTaq polymerase (Perkin-Elmer Cetus), 1 µl each of sense and antisense primer at 1 OD/ml (Butch et al. (1993) *J. Immunol.* 150: 39–47). PCR tubes were overlaid with paraffin oil and amplified for 30 cycles using a DNA Thermal Cycler (Perkin-Elmer Cetus). Each sample was denatured at 94° C. for 2 min, annealed at 55° C. for 0.5 min, and extended at 72° C. for 1 min. PCR products and markers were analyzed on a 1.7% UltraPure agarose gel (Gibco BRL) using Tris-borate buffer (Boehringer-Mannheim). Ethidium bromide (0.5 µg/ml) was incorporated into the gel in order to visualize the cDNA with UV light. Primers for HPRT were used to compare efficiency of reverse transcription for different samples.

As shown in Table 1, Pro T cells activated in vitro with PMA, A23187, and IL-1 produced mRNA for IL-2, IFN-γ, TNF-α, GM-CSF, and both the P35 and P40 chains of IL-12. No mRNA for IL-4 or IL-10 was detected. Similarly, freshly sorted Pro T cells were shown to contain mRNA for IL-2, INF-γ, TNF-α and GM-CSF. Again, no message for IL-4 or IL-10 was detected. This common mRNA cytokine profile of freshly sorted and in vitro activated Pro T cells indicates that Pro T cells are activated in vivo.

To further verify the cytokine producing potential of Pro T cells, a Southern blot of an activated Pro T cell cDNA library was probed. A Pro T cell probe cDNA library was digested with BstXI/NotI to release inserts. One µg of digest was loaded in each well of a 1 % agarose gel. cDNA inserts for each cytokine probe were electrophoresed in parallel. The gel was denatured (1.5M NaOH, 1.5M NaCl), neutralized (1.5M NaCl, 0.5M Tris pH 7.4), and transferred to GeneScreen membranes (NEN Research Products, Boston Mass.). Lanes were cut into filter strips and each strip was probed with $^{32}$P-dCTP labeled cytokine cDNA ($10^6$ cpm/ml) in hybridization buffer (1% BSA, 0.5M NaHPO$_4$ pH 7.2, 1 mM EDTA, 7% SDS) at 65° C. overnight. Filters were washed three times in 0.2×SSC, 0.1% SOS at 50° C. for 30 min. Filters were exposed to film.

As indicated in Table 2, IL-2, IL-3, GM-CSF, IFN-γ, and the P40 chain of IL-12 were detected in this library. The difference in detection between the Southern blot of the library and PCR amplification of the freshly sorted cells can be explained by the relative abundance of each cytokine mRNA. For example, the detection of TNF-α by PCR in activated Pro T cells but not by Southern blot analysis of the activated Pro T cell cDNA library may reflect either the relatively low level transcription of this mRNA under the in vitro activation conditions employed, or the different kinetics of TNF-α mRNA induction. In contrast, the detection of GM-CSF by both PCR of in vitro activated Pro T cells and Southern blot analysis of the activated Pro T cell cDNA indicates that the message for this cytokine is either abundant relative to that of TNF-α or the kinetics of induction of its mRNA differs.

TABLE 1

Cytokine producing profile of Pro T cells by Polymerase Chain Reaction. Pro T cells were sorted by FACS as described and subjected to PCR analysis as freshly sorted unactivated cells or cells activated in vitro. A positive PCR signal is indicted by (+), and no PCR signal is indicated by (−).

| Cytokine | Unactivated | Activated in vitro |
| --- | --- | --- |
| IL-2 | + | + |
| IL-4 | − | − |
| IL-10 | − | − |
| P35 | − | + |
| P40 | − | + |
| IFN-γ | + | + |
| TNF-α | + | + |
| GM-CSF | + | + |

TABLE 2

Pro T cell cDNA library was probed by Southern blot with known cytokines (21). A strong hybridization signal is indicted by (++), moderate to weak hybridization signal is indicated by (+) and no hybridization signal is indicated by (−).

| Cytokine | Hybridization |
| --- | --- |
| IL-2 | ++ |
| IL-3 | + |
| IL-4 | − |
| IL-5 | − |
| IL-6 | − |
| IL-10 | − |
| P35 | − |
| P40 | + |
| IFN-γ | ++ |
| TNF-α | − |
| GM-CSF | ++ |
| TGF-β | − |

Example 5
Comparison of Mouse lymphotactin to C-C and CXC superfamily Chemokines.

While screening the Pro T cell cDNA library a clone was isolated whose protein translation consistently matched a short carboxyl terminal segment of C-C chemokine protein chains in BLAST searches of protein and nucleic acid databases (Altschul et al. (1990) *J. Mol Biol.* 403–410). A weaker similarity in this region was also noted with C-X-C chemokine sequences. Because of its biological activities we designated this molecule Lymphotactin (LTn). cDNA clones were sequenced using double stranded templates and a sequence kit (United States Biochemicals, Cleveland, Ohio). Obtained sequences were compared to previously reported sequences in the data banks with FASTDB (Intelligenetics, Mountain View, Calif.). Lymphotactin amino acid sequence were aligned with the C-X-C chemokine Gro α and the C-C chemokine Mip-1β (Macrophage inflammatory protein 1β). A close comparison of Lymphotactin with members of both the C-C and C-X-C chemokine families yielded insight into the origins of this gene. In FIG. 1, the amino acid sequences of Mip-1β and Gro α, respectively representative of C-C and C-X-C chemokines (Davatelis et al. (1988) *J. Exp. Med.* 167: 1939–44), are displayed based on the conserved exon organization of their chemokine gene families. The Exon organization represented is based on comparison to Mip-1β. Boxed residues are homologous between the two sequences. Black boxed residues represent the four cysteines diagnostic of both the C-X-C and C-C chemokine families. In addition, the shaded boxes represent the residues which are diagnostic of the C-C chemokine family (Bairoch (1993) *Nucleic Acids Res.* 21: 3097–103).

Alignment of the Lymphotactin sequence with these molecules shows that the highest degree of identity occurs within exon three homologues. The C-C and C-X-C chemokine families are defined by two structurally conserved cysteines in their respective protein amino termini, which in turn form part of two distinct disulfide links to a carboxyl terminal located pair of cysteine residues. The Lymphotactin sequence strikingly lacks the first cysteine of the distinctive amino terminal C-C or C-X-C motifs, as well as the corresponding disulfide partner elsewhere in the chain (FIG. 1). Therefore, Lymphotactin maintains only one of the two disulfide bridges (Cys2-Cys4) of the chemokine fold (Lodi et al (1994) *Science* 263: 1762–1767. Aside from this anomaly, Lymphotactin appears to be more closely related to the C-C chemokine family as judged by sparse sequence patterns diagnostic of C-C chemokines. Specifically, a phenylalanine and a tyrosine residue (FIG. 1, shaded boxes) characteristic of the C-C chemokine family but not found in the C-X-C family is conserved in Lymphotactin.

Vertebrate chemokine genes are closely clustered on discrete chromosomes based on their C-C or C-X-C family relationship. For example, all previously reported C-C chemokines map to human chromosome seventeen and mouse chromosome eleven. Similarly, the C-X-C chemokines map to human chromosome four and based on the similarities between mouse and human chromosomes the C-X-C chemokines probably map to mouse chromosome five. Lymphotactin notably maps to the distal region of mouse chromosome one linked to Fasl, At3, Sele, and Otfl. Taken together with the sequence comparisons, these data support the hypothesis that Lymphotactin represents the structural prototype of a new chemokine class.

Example 6
Mapping of Mouse Lymphotactin to chromosome 1

Note that the Lymphotactin gene is indicated by LTn, the Fas ligand gene by Fas1, the antithrombin 3 gene by At3, the selectin endothelium gene by sele (formerly Elam), and the octamer binding transcription factor 1 gene by Otf1 in the following discussion.

LTn maps in the distal region of mouse chromosome one. LTn was placed on mouse chromosome one by interspecific backcross analysis. Interspecific backcross progeny were generated by mating [(C57BL/6J×Mus Spretus)F$_1$ females and C57BL/6J] males as described (Copeland et al (1991) Trends Genet. 7: 113–118. A total of 205 F$_2$ mice were used to map the LTn locus. DNA isolation, restriction enzyme digestion, agarose gel electrophoresis, Southern blot transfer and hybridization were performed according to standard techniques (Jenkins et al (1982) *J. Virol.* 43: 26–36. All blots were prepared with Hybond-N nylon membrane (Amersham). The probe, a 536 base pair fragment of mouse LTn cDNA, was labeled with 32$^P$×dCTP; washing was done to a final stringency of 0.1×SSC, 0.1% SDS, 65° C. A fragment of 13.0 kb was detected in SphI digested C57BL/6J DNA and a fragment of 8.6 kb was dejected in SphI digested M. spretus DNA. The presence or absence of the 8.6 kb M. spretus-specific SphI fragment was followed in backcross mice.

Recombination distances were calculated using the computer program SPRETUS MADNESS (National Cancer Institute Frederick Cancer Center, Frederick Md.). Gene order was determined by minimizing the number of recombination events required to explain the allele distribution patterns. The ratios of the total number of mice exhibiting recombinant chromosomes to the total number of mice analyzed for each pair of loci and the most likely gene order are: centromere - Fast - 0/180 - At3 - 3/164 - Sele- 2/162 - LTn - 1/170 - Otf1. The recombination frequencies (expressed as genetic distances in centimorgans (cM)+/− the standard error) are — [Fasl, At3]-1.8+/−1.1-Sele-1.2+/−0.9-LTn -0.6+/−0.6-Otf1. Table 3 shows the segregation patterns of LTn and flanking genes in 154 backcross animals that were typed for all loci are shown. For individual pairs of loci, more than 154 animals were typed. Each column represents the chromosome identified in the backcross progeny that was inherited from the (C57BL/6J×M. spretus) F1 parent. The shaded boxes represent the presence of a C57BL/6J allele and white boxes represent the presence of M. spretus allele. The number of offspring inheriting each type of chromosome is listed at the bottom of each column. A partial chromosome one linkage map showing the location of LTn in relation to linked genes is described at the bottom of Table 3. Recombination distances between loci in centiMorgans are described, and the positions of the loci in human chromosomes, where known, are also given. References for the human map positions of loci cited in this study can be obtained from GDB (Genome Data Base), a computerized database of human linkage information maintained by The William H. Welch Medical Library of The Johns Hopkins University (Baltimore, Md.).

TABLE 3

Gene mapping of Mouse Lymphotactin

| Gene | | | | | | | | | | |
|---|---|---|---|---|---|---|---|---|---|---|
| Fas1 | ■ | □ | □ | ■ | □ | ■ | □ | ■ | □ | ■ |
| At3 | ■ | □ | ■ | □ | □ | ■ | □ | ■ | □ | ■ |
| Sele | ■ | □ | ■ | □ | ■ | □ | □ | ■ | □ | ■ |
| Ltn | ■ | □ | ■ | □ | ■ | □ | ■ | □ | □ | ■ |
| Otf1 | ■ | □ | ■ | □ | ■ | □ | ■ | □ | ■ | □ |
| | 64 | 84 | 0 | 0 | 2 | 1 | 0 | 2 | 1 | 0 |

In humans, Fas1 and At3 are located at 1 q23–q25.1; Sele is located at 1 q22–q25; and Otf1 is located at 1 cen–q32. Mouse Ltn maps between Sele and Otf1 on mouse chromosome 1 at a position 1.2 centiMorgans from Sele and 0.6 centiMorgans from Otf1. Ltn maps to a position 3 centiMorgans from Fas1 and At3.

Example 7
Expression of Mouse Lymphotactin Protein in *E. coli*.

PCR was used to mutagenize the Lymphotactin cDNA in order to insert a HindIII restriction site proximal to Gly2 (1 being the expected N-terminal residue of the mature secreted protein) and an XhoI site distal to the translation stop codon of the open reading frame. The resulting HindIII/XhoI fragment was inserted into HindIII and XhoI cleaved pFLAG-1 plasmid (International Biotechnologies, New Haven, Conn.). The resulting expression plasmid was transformed into the Topp5 *E.coli* strain (Stratagene, La Jolla, Calif.) and ampicillin resistant (50 µg/ml) transformants were grown in Luria Broth (Gibco) at 37° C. until the optical density at 550 nm was 0.7. Recombinant protein was induced with 0.4 mM isopropyl-βD-thiogalactopyranoside (Sigma, St. Louis, Mi.) and incubation of the cells continued at 20° C. for a further 18 hours. Cells from a 1 liter culture were harvested by centrifugation and resuspended in 200 ml of ice cold 30% sucrose, 50 mM Tris HCI pH 8.0, 1 mM ethylenediaminetetraacetic acid. After 10 min on ice, ice cold water was added to a total volume of 2 liters. After 20 min on ice, cells were removed by centrifugation and the supernatant was clarified by filtration via a 5µM Millipak 60 (Millipore Corp., Bedford, Mass.). The recombinant protein was purified via a 25 ml M2 affinity matrix (International Biotechnologies) after cycling at 200 ml/hour for 48 hours at 4° C., washing with phosphate buffered saline, elution with 0.1M glycine HCl pH 3.0, and neutralization with Tris HCl to pH 8.0.

Example 8
Biological Activity of Mouse Lymphotactin

Recombinant lymphotactin was generated by expression in *E. coli* as shown in Example 7 above, and tested for biological activity. In general, when C-C chemokines bind their receptor on leukocytes there is a measurable intracellular $Ca^{2+}$flux (Neote et al. (1993) *Cell* 72,415–25). Therefore, we examined the ability of Lymphotactin to initiate calcium flux in THP-1 cells, a human monocytic cell line that is responsive to mouse Mip-1α and most other mouse and human C-C and C-X-C chemokines (THP-1 cells are available from ATCC in the Tumor Immunology Bank under accession number TIB 203). The assay used is termed an intra-cellular $Ca^{+2}$ flux assay. THP-1 cells were loaded in the presence of 3 µM indol-1 AM (Calbiochem). Fluorescence was measured on a PTI spectrofluorometer at an excitation wavelength of 350 nm. Dual simultaneous emissions were recorded at 400 and 490 nm. Ratios were calculated at two points per second. The Fluorescence ratio was calculated at 400/490 nm. Unlike Mip-1α, mouse lymphotactin was unable to generate a calcium flux in THP-1 cells. This result suggests that Lymphotactin may employ a receptor that is not used by other known chemokines. This possibility is further strengthened by the data presented herein for human lyphotactin, which show that lymphotactin does cause an intracellular calcium flux in human PBL.

Another defining characteristic of chemokines is their ability to induce a chemotactic response in cells of the immune system. A cell type will demonstrate chemotaxis to a relatively narrow concentration range of chemokine in vitro, where a high concentration causes adhesion and a low concentration will not elicit chemotaxis (Zigmond et al. (1973) *J. Exp. Med.* 137: 387–410). In order to assess the chemotactic abilities of Lymphotactin, several leukocyte populations were tested for their ability to migrate in response to Lymphotactin using a thymokine cell chemotaxis assay. A variety of cells demonstrate a dose dependent chemotactic response to Lymphotactin. Among the most responsive cell type was CD8+thymocytes where a concentration of $10^{-10}$M induced chemotaxis. In contrast, a concentration of $10^{-8}$M was required to induce a chemotactic response from thymic CD4+cells. This parallels the response of these two cell types to the chemokine Mip-1α. Comparable to the thymic CD4+chemotactic response to Lymphotactin were the responses by T cell depleted spleen cells, day 15 fetal liver cells, bone marrow cells, and lymph node cells. These cell populations demonstrated a similar chemotactic response to MIP-1α. However, unlike Mip-1α, Lymphotactin did not induce a chemotactic response to either peritoneal exudate cells or the human monocytic cell line THP-1. Further analysis of monocyte/macrophage populations derived from a variety of sources as well as neutrophils supported the conclusion that Lymphotactin does not induce chemotaxis in monocyte/macrophage or neutrophils. Therefore, Lymphotactin is unique among chemokines in that it only induces chemotactic responses in lymphoid populations.

Thymokine cell chemotaxis assays were performed using 48-well microchemotaxis apparatus using standard techniques (Bacon et al. (1988) *Br. J. Pharmacol.* 95: 966–74). Migration was measured as cell number per 5 high power fields (×400) with duplicate wells being counted for each of three experiments. All cells were obtained from Balb/c mice unless noted otherwise. Qualitative interpretation of the significance of the chemotactic response in comparing one cell population to another is determined by several characteristics: the absolute number of cells that demonstrate chemotaxis, the concentration of factor that elicits the maximum chemotactic response; and the difference in number of cells that chemotax from the least to the most optimal concentration.

Example 9
Isolation of Human Lymphotactin

Human Lymphotactin shares 60% amino acid identity to mouse LTn. It resembles its mouse counterpart in many aspects, including the ability to chemoattract T cells but not monocytes.

Human cDNA clones encoding LTn were identified by screening a library, generated from the CD8+T cell clone A10 (Cocks et al. (1993) *Int. Immunol.* 5: 657, with the mouse LTn cDNA as probe. Construction the cDNA library has been described previously (Cocks et al., supra). The library was screened by standard methods (Maniatis et al. 1982), using the mouse LTn cDNA as a probe. Four different cDNA clones for LTn were isolated, representing 730bp, 625bp, 562bp and 520bp species.

The entire cDNA of human Lymphotactin was sequenced by the dideoxynucleotide chain termination method with T7 polymerase (U.S. Biochemicals, Cleveland, Ohio) using double-stranded DNA as template. Data base searching and sequence analysis were performed using IntelliGenetics programs (Mountain View, Calif.).

All of these clones contained identical open reading frames of 114 amino acids (with the exception of the 625bp species, which had two conservative amino acid changes at the N-terminal sequence) but differed in the length of their 3' untranslated regions. The 562bp and 520bp clones were the most predominant in the library. Only two clones were represented by the 625bp species and one clone by the 730bp species. The 3' untranslated region of the cDNA contains two polyadenylation signal sites. The 625bp and 520bp clones use the first polyadenylation signal site, while the 730bp species uses the second but contains a 180bp insertion upstream of the first that contains two more polyadenylation signal sites.

Example 10
Comparison of Human Lymphotactin with the C-C Chemokines

Comparison of the amino acid sequence deduced from the human cDNA clone with mouse LTn revealed that they share 60% sequence identity. The two thymokines are of similar size, with the human LTn having a predicted molecular weight of about 12,000 daltons and the mouse LTn having a predicted molecular mass of about 11,500 daltons, (excluding any glycosylation for either molecule). When the protein sequence of human lymphotactin is compared to the Swiss Protein Data Base, the C-C chemokine family members monocyte chemotactic protein-2 (MCP-2) and macrophage inflammatory protein-1α(Mip-1α) are identified as sharing significant homology to human lymphotactin (human LTn). Therefore, like mouse LTn, human LTn shares the highest amino acid identity with the C-C chemokines, especially in the region corresponding to exon 3. Human LTn is also lacking the first and third cysteine residues that would pair to form one of two disulfide bridges characteristic of the C-C and C-X-C chemokine families (Lodi et al. 1994).

Interestingly, there is a high degree of homology in the tail region of mouse and human LTn. Although a similar C-terminal extension can be found in mouse MCP-1 (Rollins et al. 1988), this tail region has been lost in the human counterpart (Chang et al 1989; Furutani et al. 1989; Yoshimura et al 1999). Thus, LTn is the first example of a human chemokine which has conserved this tail region.

Example 11
Expression and Distribution of human LTn mRNA

Total RNA from sorted CD8+thymocytes, sorted CD4+ thymocytes, the Th1 clone TA20, and the Th2 clone NP44 was prepared using the RNAzol B method (TM Cinna Scientific Inc., Friendswood, Tex). The RNA samples were fractionated on 0.85% denaturing agarose gels and transferred to BA-S nitrocellulose (Schleicher and Schuell, Keone, NH) as described (Cocks et al 1993). RNA from spleen, thymus, prostate, testis, ovary, small intestine, colon, and peripheral blood leukocytes was purchased as a northern blot from Clontech (Palo Alto, Calif.). Filters were hybridized with a Xmnl-Pvull fragment of pJFEhLTn which contains the LTn coding region.

The expression pattern for human LTn mRNA is very similar to that of mouse LTn. Activated CD8+thymocytes express LTn while activated CD4+thymoctyes have undetectable levels of LTn. Human LTn is also abundantly expressed in an activated Th1 clone but only expressed at very low levels in an activated Th2 clone. Human LTn mRNA was detected in resting spleen, thymus, small intestine and peripheral blood leukocytes (PBL) at fairly high levels and at much lower levels in prostate and ovary tissues.

Example 12
Production of Recombinant hLTn

A bacterial expression plasmid containing human LTn cDNA was constructed. The cDNA was mutagenized using Polymerase Chain Reaction (PCR) to insert a HindIII restriction site proximal to the Val residue of the mature protein and an Xhol site distal to the translation stop codon of the open reading frame so that the resulting fragment could be subcloned into the pFLAG-1 plasmid (International Biotechnologies, New Haven, Conn.) The expression plasmid was transformed into the Topp5 *E.coli* stain (Stratagene, La Jolla, Calif.) and recombinant protein was induced and purified as previously described above. Fractions were collected and pooled.

Example 13
Biological Properties of Human Lymphotactin

The chemotactic activity (determined as described above for mouse lymphotactin) of human LTn was measured by its effect on the migration of lymphocyte populations using the above described cell chemotaxis assay. Human LTn induced chemotaxis in human $CD8^+$ and $CD4^+$ T cell clones at similar concentrations to those shown to induce a chemotactic response in, $CD8^+$ and $CD4^+$ thymocytes when using mouse LTn (see above). $CD8^+$ T cells were responsive at a concentration of $10^{-10}$ M and $CD4^+$ T cells at $10^{-7}$ M LTn. Human monocytes were not responsive to human LTn.

Ability of LTn to Induce a $Ca^{++}$ Flux

The measurement of an intracellular $Ca^{++}$ flux is generally an indicator of leukocyte receptor binding by chemokines and it can be used to predict whether various chemokines signal through the same or different receptors. Intra cellular $Ca^{+2}$ flux assays were used to monitor the effects of human lymphotactin on cell populations as described above for mouse lymphotactin. Human peripheral blood leukocytes were loaded in the presence of the calcium indicator 3 µM indol-1 AM (Calbiochem, San Diego, Calif.) and then challenged with LTn or a combination of LTn and IL8. Fluorescence was measured on a PTI spectrofluorometer at an excitation wavelength of 350 nm. Simultaneous emissions were recorded at 400 and 490 nm and ratios were calculated at two points per second.

When recombinant LTn was used to induce intracellular $Ca^{++}$ flux in human PBL, a clear rise in intracellular $Ca^{++}$ concentration was observed. In addition, a second calcium flux was observed when IL8 was added following LTn treatment, suggesting that LTn uses a different receptor from IL8. Similar results were obtained when C-C chemokines were added after LTn treatment.

Example 14
Isolation of a Receptor for a Mouse Thymokine

A thymokine can be used as a specific binding reagent, by taking advantage of its specificity of binding, much like an antibody would be used. A binding reagent is either labeled as described above, e.g., fluorescence or otherwise, or immobilized to a substrate for panning methods.

The binding composition is used to screen an expression library made from a cell line which expresses a thymokine. Standard staining techniques are used to detect or sort intracellular or surface expressed ligand, or surface expressing transformed cells are screened by panning. Screening of intracellular expression is performed by various staining or immunofluorescence procedures. See also McMahan et al (1991) *EMBO J.* 10: 2821-2832.

For example, on day 0, precoat 2-chamber permanox slides with 1 ml per chamber of fibronectin, 10 ng/ml in PBS, for 30 min at room temperature. Rinse once with PBS. Then plate COS cells at $2-3\times10^5$ cells per chamber in 1.5 ml of growth media. Incubate overnight at 37° C.

On day 1 for each sample, prepare 0.5 ml of a solution of 66 mg/ml DEAE-dextran, 66 mM chloroquine, and 4 mg DNA in serum free DME. For each set, a positive control is prepared, e.g., of mouse thymokine-FLAG cDNA at 1 and ¹⁄₂₀₀ dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin(0. 1%) with 32 ml/ml of 1 M $NaN_3$ for 20 min. Cells are then washed with HBSS/saponin 1×. Add thymokine or thymokine/antibody complex to cells and incubate for 30 min. Wash cells twice with HBSS/saponin. If appropriate, add first antibody for 30 min. Add second antibody, e.g., Vector anti-mouse antibody, at ¹⁄₂₀₀ dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin.

Wash cells twice with HBSS/saponin. Add ABC HRP solution and incubate for 30 min.

Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85°–90° C.

Alternatively, thymokine reagents are used to affinity purify or sort out cells expressing a receptor. See, e.g., Sambrook et al or Ausubel et al Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a thymokine fusion construct, or by use of antibodies raised against the first antibodies. Recursive cycles of selection and amplification lead to enrichment of appropriate clones and eventual isolation of ligand expressing clones.

Phage expression libraries can be screened by thymokine. Appropriate label techniques, e.g., anti-FLAG antibodies, will allow specific labeling of appropriate clones.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

SEQUENCE SUBMISSION

SEQ ID NO: 1 is mouse m3C9 thymokine clone nucleotide sequence.

SEQ ID NO: 2 is corresponding mouse thymokine amino acid sequence.

SEQ ID NO: 3 is human A 10- 4 thymokine clone nucleotide sequence.

SEQ ID NO: 4 is corresponding human thymokine amino acid sequence.

What is claimed is:

1. An isolated nucleic acid encoding a mammalian thymokine of approximately 11,000 to 12,500 daltons in the unglycosylated form, wherein said thymokine protein:
   i. specifically binds to polyclonal antibodies generated against an immunogen selected from the group consisting of:
      a) the polypeptide of SEQ ID NO. 2; and
      b) the polypeptide of SEQ ID NO. 4; and
   ii. has the following chemical properties;
      a) the ability to induce a dose-dependent chemotactic response by thymocytes in a thymokine cell chemotaxis assay;
      b) the inability to induce a dose-dependent chemotactic response in human THP-1 cells in said thymokine cell chemotaxis assay; and
      c) the inability to induce an intracellular $Ca^{+2}$ flux in human THP-1 cells in an intracellular $Ca^{+2}$ flux assay.

2. An isolated nucleic acid of claim 1 wherein the nucleic acid encodes the amino acid sequence of SEQ ID NO. 2.

3. An isolated nucleic acid of claim 1 wherein the nucleic acid encodes the amino acid sequence of SEQ ID NO. 4.

4. An isolated nucleic acid of claim 1 consisting of the coding sequence selected from the group consisting of SEQ ID NO. 1 and 3.

5. An isolated nucleic acid of claim 1 wherein the nucleic acid is joined to a recombinant vector.

6. An isolated nucleic acid of claim 1 wherein the nucleic acid is contained within a cell able to express the thymokine encoded by the nucleic acid.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 536 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 32..373

( x i ) SEQUENCE DESCRIPTION: SEQ ID NO:1:

```
TGTGCTGGAA AGGGCCAGCA AGACCTCAGC C ATG AGA CTT CTC CTC CTG ACT              52
                                  Met Arg Leu Leu Leu Leu Thr
                                   1               5

TTC CTG GGA GTC TGC TGC CTC ACC CCA TGG GTT GTG GAA GGT GTG GGG            100
Phe Leu Gly Val Cys Cys Leu Thr Pro Trp Val Val Glu Gly Val Gly
         10                  15                  20

ACT GAA GTC CTA GAA GAG AGT AGC TGT GTG AAC TTA CAA ACC CAG CGG            148
Thr Glu Val Leu Glu Glu Ser Ser Cys Val Asn Leu Gln Thr Gln Arg
 25                  30                  35

CTG CCA GTT CAA AAA ATC AAG ACC TAT ATC ATC TGG GAG GGG GCC ATG            196
Leu Pro Val Gln Lys Ile Lys Thr Tyr Ile Ile Trp Glu Gly Ala Met
 40                  45                  50                  55

AGA GCT GTA ATT TTT GTC ACC AAA CGA GGA CTA AAA ATT TGT GCT GAT            244
Arg Ala Val Ile Phe Val Thr Lys Arg Gly Leu Lys Ile Cys Ala Asp
             60                  65                  70

CCA GAA GCC AAA TGG GTG AAA GCA GCG ATC AAG ACT GTG GAT GGC AGG            292
Pro Glu Ala Lys Trp Val Lys Ala Ala Ile Lys Thr Val Asp Gly Arg
         75                  80                  85

GCC AGT ACC AGA AAG AAC ATG GCT GAA ACT GTT CCC ACA GGA GCC CAG            340
Ala Ser Thr Arg Lys Asn Met Ala Glu Thr Val Pro Thr Gly Ala Gln
         90                  95                 100

AGG TCC ACC AGC ACA GCG ATA ACC CTG ACT GGG TAACAGCCTC CAGGACAATG          393
Arg Ser Thr Ser Thr Ala Ile Thr Leu Thr Gly
 105                 110

TTTCCTCACT CGTTAAGCAG CTCATCTCAG TTCCCAAACC CATTGCACAA ATACTTATTT          453

TTATTTTTAA CGACATTCAC ATTCATTTCA AATGTTATAA GTAATAAATA TTTATTATTG          513

AAAAAAAAAA AAAAAAAAA AAA                                                   536
```

( 2 ) INFORMATION FOR SEQ ID NO:2:

( i ) SEQUENCE CHARACTERISTICS:
    ( A ) LENGTH: 114 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Arg Leu Leu Leu Leu Thr Phe Leu Gly Val Cys Cys Leu Thr Pro
 1               5                  10                  15

Trp Val Val Glu Gly Val Gly Thr Glu Val Leu Glu Glu Ser Ser Cys
             20                  25                  30
```

|  |  |  |  |  |  |  |  |  |  |  |  |  |  |  |
|---|---|---|---|---|---|---|---|---|---|---|---|---|---|---|
| Val | Asn | Leu | Gln | Thr | Gln | Arg | Leu | Pro | Val | Gln | Lys | Ile | Lys | Thr | Tyr |
|  |  | 35 |  |  |  | 40 |  |  |  | 45 |  |  |  |  |
| Ile | Ile | Trp | Glu | Gly | Ala | Met | Arg | Ala | Val | Ile | Phe | Val | Thr | Lys | Arg |
|  | 50 |  |  |  | 55 |  |  |  | 60 |  |  |  |  |  |
| Gly | Leu | Lys | Ile | Cys | Ala | Asp | Pro | Glu | Ala | Lys | Trp | Val | Lys | Ala | Ala |
| 65 |  |  |  | 70 |  |  |  | 75 |  |  |  |  |  | 80 |
| Ile | Lys | Thr | Val | Asp | Gly | Arg | Ala | Ser | Thr | Arg | Lys | Asn | Met | Ala | Glu |
|  |  |  | 85 |  |  |  | 90 |  |  |  | 95 |  |  |  |
| Thr | Val | Pro | Thr | Gly | Ala | Gln | Arg | Ser | Thr | Ser | Thr | Ala | Ile | Thr | Leu |
|  |  | 100 |  |  |  | 105 |  |  |  | 110 |  |  |  |  |
| Thr | Gly |

( 2 ) INFORMATION FOR SEQ ID NO:3:

( i ) SEQUENCE CHARACTERISTICS:
    ( A ) LENGTH: 562 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 15..356

( x i ) SEQUENCE DESCRIPTION: SEQ ID NO:3:

```
GCGGGACCTC AGCC ATG AGA CTT CTC ATC CTG GCC CTC CTT GGC ATC TGC                50
              Met Arg Leu Leu Ile Leu Ala Leu Leu Gly Ile Cys
                1          5                    10

TCT CTC ACT GCA TAC ATT GTG GAA GGT GTA GGG AGT GAA GTC TCA GAT                98
Ser Leu Thr Ala Tyr Ile Val Glu Gly Val Gly Ser Glu Val Ser Asp
         15              20                  25

AAG AGG ACC TGT GTG AGC CTC ACT ACC CAG CGA CTG CCG GTT AGC AGA                146
Lys Arg Thr Cys Val Ser Leu Thr Thr Gln Arg Leu Pro Val Ser Arg
     30                  35                  40

ATC AAG ACC TAC ACC ATC ACG GAA GGC TCC TTG AGA GCA GTA ATT TTT                194
Ile Lys Thr Tyr Thr Ile Thr Glu Gly Ser Leu Arg Ala Val Ile Phe
 45                  50                  55                  60

ATT ACC AAA CGT GGC CTA AAA GTC TGT GCT GAT CCA CAA GCC ACG TGG                242
Ile Thr Lys Arg Gly Leu Lys Val Cys Ala Asp Pro Gln Ala Thr Trp
             65              70                  75

GTG AGA GAC GTG GTC AGG AGC ATG GAC AGG AAA TCC AAC ACC AGA AAT                290
Val Arg Asp Val Val Arg Ser Met Asp Arg Lys Ser Asn Thr Arg Asn
             80              85                  90

AAC ATG ATC CAG ACC AAG CCA ACA GGA ACC CAG CAA TCG ACC AAT ACA                338
Asn Met Ile Gln Thr Lys Pro Thr Gly Thr Gln Gln Ser Thr Asn Thr
         95                  100                 105

GCT GTG ACC CTG ACT GGC TAGTAGTCTC TGGCACCCTG TCCGTCTCCA                       386
Ala Val Thr Leu Thr Gly
         110

GCCAGCCAGC TCATTTCACT TTACACCCTC ATGGACTGAG TTTATACTCA CCTTTTATGA              446

AAGCACTGCA TGAATAAAAT TATTCCTTTG TATTTTACT  TTTAAATGTC TTCTGTATTC              506

ACTTATATGT TCTAATTAAT AAATTATTTA TTATTAAGAA TAAAAAAAA AAAAAA                   562
```

( 2 ) INFORMATION FOR SEQ ID NO:4:

( i ) SEQUENCE CHARACTERISTICS:
    ( A ) LENGTH: 114 amino acids
    ( B ) TYPE: amino acid
    ( D ) TOPOLOGY: linear (ii) MOLECULE TYPE: protein (xi) SEQUENCE DESCRIPTION: SEQ ID NO:4:

```
Met Arg Leu Leu Ile Leu Ala Leu Leu Gly Ile Cys Ser Leu Thr Ala
 1               5                  10                  15
Tyr Ile Val Glu Gly Val Gly Ser Glu Val Ser Asp Lys Arg Thr Cys
            20                  25                  30
Val Ser Leu Thr Thr Gln Arg Leu Pro Val Ser Arg Ile Lys Thr Tyr
            35                  40                  45
Thr Ile Thr Glu Gly Ser Leu Arg Ala Val Ile Phe Ile Thr Lys Arg
    50                  55                  60
Gly Leu Lys Val Cys Ala Asp Pro Gln Ala Thr Trp Val Arg Asp Val
65                  70                  75                  80
Val Arg Ser Met Asp Arg Lys Ser Asn Thr Arg Asn Asn Met Ile Gln
                85                  90                  95
Thr Lys Pro Thr Gly Thr Gln Gln Ser Thr Asn Thr Ala Val Thr Leu
                100                 105                 110
Thr Gly
```